(12) United States Patent
Averett et al.

(10) Patent No.: US 6,924,271 B2
(45) Date of Patent: Aug. 2, 2005

(54) 3-β-D-RIBOFURANOSYLTHIAZOLO[4-5-D] PYRIDIMINE NUCLEOSIDES AND USES THEREOF

(75) Inventors: Devron R. Averett, Cardiff by the Sea, CA (US); Stephen E. Webber, San Diego, CA (US); Joseph R. Lennox, Cardiff by the Sea, CA (US); Erik J. Rueden, Santee, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/305,061

(22) Filed: Nov. 27, 2002

(65) Prior Publication Data

US 2003/0199461 A1 Oct. 23, 2003

Related U.S. Application Data

(60) Provisional application No. 60/333,460, filed on Nov. 27, 2001.

(51) Int. Cl.$^7$ .......................... A61K 31/70; C07H 19/02; C07H 19/14
(52) U.S. Cl. ..................... 514/43; 514/263.37; 514/274; 514/265.1; 514/388; 514/45; 514/63; 536/26.7; 536/26.8; 536/27.14; 536/27.4; 536/27.6; 536/28.5; 536/26.23; 536/26.26; 536/27.13; 536/27.81; 536/28.2; 536/28.51; 536/4.1; 536/27.21; 544/244; 544/276; 544/314
(58) Field of Search ............................. 514/43, 263.37, 514/274, 265.1, 388, 45, 63; 536/26.7, 26.8, 27.14, 27.4, 27.6, 28.5, 26.23, 26.26, 27.13, 27.81, 28.2, 28.51, 4.1, 27.21; 544/244, 276, 314

(56) References Cited

U.S. PATENT DOCUMENTS

| | | | |
|---|---|---|---|
| 4,746,651 A | 5/1988 | Goodman | |
| 4,880,784 A | 11/1989 | Robins et al. | |
| 5,041,426 A | 8/1991 | Robins et al. | |
| 5,248,672 A | 9/1993 | Townsend et al. | |
| 5,424,295 A | 6/1995 | Krenitsky et al. | |
| 5,492,897 A | 2/1996 | Krenitsky et al. | |
| 6,479,463 B1 | 11/2002 | Wang et al. | |
| 6,509,320 B1 * | 1/2003 | Wang et al. | 514/43 |
| 6,566,344 B1 * | 5/2003 | Gosselin et al. | 514/45 |
| 2002/0058635 A1 | 5/2002 | Averett | |

FOREIGN PATENT DOCUMENTS

| | | | |
|---|---|---|---|
| WO | WO 89/05649 | * | 6/1989 |
| WO | WO 92/16215 A1 | | 10/1992 |
| WO | WO 94/17090 A1 | | 8/1994 |

OTHER PUBLICATIONS

Purifoy et al. J. of Medical Virology Supplement, 1:139–145, 1993.*

International Search Report mailed Mar. 18, 2003 for PCT/US02/38001.

Daskalov et al., "Synthesis and Properties of O$^6$-Substituted Guanosine Derivatives," *Bull. Chem. Soc. Jpn.*, 54(10):3076–3083 (1981).

(Continued)

Primary Examiner—James O. Wilson
Assistant Examiner—Devesh Khare
(74) Attorney, Agent, or Firm—Connolly Bove Lodge & Hutz, LLP; Mark J. Pino, Esq.

(57) ABSTRACT

The invention is directed to 3-β-D-ribofuranosylthiazolo[4,5-d]pyridimine nucleosides and pharmaceutical compositions containing such compounds that have immunomodulatory activity. The invention is also directed to the therapeutic or prophylactic use of such compounds and compositions, and to methods of treating diseases and disorders described herein, by administering effective amounts of such compounds.

10 Claims, 1 Drawing Sheet

OTHER PUBLICATIONS

Goodman, "Role of Salvage and Phosphorylation in the Immunostimulatory Activity of C8–Substituted Guanine Ribonucleosides," *J. Immunol.* 141(7):2394–2399 (1988).

Fathi et al., "Synthesis of 6–Substitued 2'–Deoxyguanosine Derivatives Using Trifluoroacetic Anhydride in Pyridine," *Tetrahedron Letters*, 31(3):319–322 (1990).

Hall et al., Aldehyde Oxidase from Rabbit Liver: Specificity Toward Purines and Their Analogs, *Archives of Biochemistry and Biophysics*, 251(1):36–46 (1986).

Jones et al., "Di–and Triester Prodrugs of the Varicella–Zoster Antiviral Agent 6–Methoxypurine Arabinoside", *J. Med. Chem.*, 35(1):56–63 (1992).

Kini et al., "Synthesis and Antiviral Activity of Certain Guanosine Analogues in the Thiazolo[4,5–d]pyrimidine Ring System," *J. Med. Chem.*, 34(10):3006–3010 (1991).

Krasny et al., "Metabolism and Pharmacokinetics of a Double Prodrug of Ganciclovir in the Rat and Monkey," *Drug Metabolism and Disposition*, 23(11):1242–1247 (1995).

Krasny, et al., "Allopurinol as an Inhibitor of the in vivo Formation of Acyclovir from Desciclovir," *Biochem. Pharm.*, 35(23):4339–4340 (1986).

Krenitsky, et al., "6–Deoxyacyclovir: A xanthine oxidase–activated prodrug of acyclovir," *Proc. Natl. Acad. Sci.*, 81:3209–3213 (1984).

Krenitsky, et al., "Xanthine Oxidase from Human Liver: Purification and Characterization," *Archives of Biochemistry and Biophysics*, 247(1):108–119 (1986).

Nagahara et al., "Thiazolo[4,5–d] pyrimidine Nucleosides. The Synthesis of Certain 3–β–D–Ribofuranosylthiazolo[4,5–d]pyrimidines as Potential Immunotherapeutic Agents,"*J. Med. Chem.*, 33(1):407–415 (1990).

Purifoy et al., "Review of Research Leading to New Anti–Hrpesvirus Agents in Clinical Development: Valaciclovir Hydrochloride (256U, the L–Valyl Ester of Acyclovir) and 882C, a Specific Agent for Varicella Zoster Virus," *Journal of Medical Virology Supplement*, 1:139–145 (1993).

Reitz, et al., "Small–Molecule Immunostimulants. Synthesis and Activity of 7,8–Disubstituted Guanosines and Structurally Related Compounds," *J. Med Chem.*, (37):3561–3578 (1994).

Revankar et al., "Thiazolo[4,5–d]Pyrimidines. Part II. Synthesis and Anti–human Cytomegalovirus Activity in Vitro of Certain Acyclonucleosides and Acyclonucleotides Derived from the Guanine Analogue 5–Aminothiazolo[4,5–d]Pyrimindine–2,7(3H,6H)–dione," *Antiviral Chemistry & Chemotherapy*, 9:53–63 (1998).

Rida et al., "Synthesis of Novel Thiazolo[4,5–d]Pyrimidine Derivatives for Antimicrobial, Anti–HIV Anticancer Investigation," *Pharmazie*, 51(12):927–931 (1996).

Seela et al., "Alternating d(G–C)$_3$ and d(C–G)$_3$ Hexanucleotides Containing 7–Deaza–2'–deoxyguanosine or 8–Aza–7–deaza–2'–deoxyguanosine in Place of dG," *Nucleic Acids Res.*, 17(3):901–910 (1989).

Smee et al., "Broad Spectrum In Vivo Antiviral Activity of 7–Thia–8–Oxoguanoine, a Novel Immunopotentiating Agent," *Antimicrobial Agents and Chemotherapy*, 33(9):1487–1492 (1989).

Smee et al., "Broad–Spectrum Activity of 8–chloro–7–deazaguanosine Against RNA Virus Infections in Mice and Rats," *Antiviral Res.*, 26:203–209 (1995).

Wong et al., "Photochemical Synthesis of 8–Hydroxyguanine Nucleosides," *Methods Enzymol*, 234:59–65 (1994).

\* cited by examiner

3-β-D-RIBOFURANOSYLTHIAZOLO[4-5-D] PYRIDIMINE NUCLEOSIDES AND USES THEREOF

This application claims the benefit of U.S. Provisional Patent Application No. 60/333,460, filed on Nov. 27, 2001.

FIELD OF THE INVENTION

The invention is directed to 3-β-D-ribofuranosylthiazolo [4,5-d]pyrimidine nucleosides and pharmaceutical compositions containing such compounds that have immunomodulatory activity. The invention is also directed to the therapeutic or prophylactic use of such compounds and compositions, and to methods of treating diseases and disorders described herein, by administering effective amounts of such compounds.

BACKGROUND OF THE INVENTION

The last few decades have seen significant efforts expended in exploring possible therapeutic uses of D- and L-purine nucleoside analogs. A number of nucleoside analogs are currently being marketed as antiviral drugs, including the HIV reverse-transcriptase inhibitors (AZT, ddI, ddC, d4T, and 3TC).

A variety of D- and L-purine nucleoside analogs have also been explored in search of immunomodulators. Guanosine analogs having substituents at the 7- and/or 8-positions, for example, have been shown to stimulate the immune system. See Reitz et al, *J. Med. Chem.*, 37, 3561–78 (1994); Michael et al., *J. Med. Chem.*, 36, 3431–36 (1993). In other research, U.S. Pat. No. 5,821,236 to Krenitsky et al. discloses 6-alkoxy derivatives of arabinofuranosyl purine derivatives that are useful for tumor therapy. Also reported in U.S. Pat. No. 5,539,098 to Krenitsky et al. are inhibitors of varicella zoster virus, including 5'-O-proprionyl and 5'-O-butyryl esters of 2-amino-6-methoxy-9-(β-D-arabinofuranosyl)-9H-purine. 7-Deazaguanosine and analogs have been shown to exhibit antiviral activity in mice against a variety of RNA viruses, even though the compound lacks antiviral properties in cell culture. 3-Deazaguanine nucleosides and nucleotides have also demonstrated significant broad spectrum antiviral activity against certain DNA and RNA viruses. Revankar et al., *J. Med. Chem.*, 27, 1489–96 (1984). Certain 7- and 9-deazaguanine C-nucleosides exhibit the ability to protect against a lethal challenge of Semliki Forest virus. Girgis et al., *J. Med. Chem.*, 33, 2750–55 (1990). Selected 6-sulfenamide and 6-sulfinamide purine nucleosides are disclosed in U.S. Pat. No. 4,328,336 to Robins et al. as having demonstrated significant antitumor activity.

Certain pyrimido [4,5-d]pyrimidine nucleosides are disclosed in U.S. Pat. No. 5,041,542 to Robins et al. as being effective in treatment against L1210 in BDFI mice. These particular nucleosides were suggested to be as a result of the role as immunomodulators. See Bonnet et al., *J Med. Chem.*, 36, 635–53 (1993). Also, Wang et al. (WIPO International Publication No. WO 98/16184) report that purine L-nucleoside compounds and analogs thereof were used to treat an infection, infestation, a neoplasm, an autoimmune disease, or to modulate aspects of the immune system. In addition, 3-β-D-ribofuranosylthiazolo [4,5-d]pyrimidine demonstrating significant immunoactivity, including murine spleen cell proliferation and in vivo activity against Semilki Forest virus, are disclosed in U.S. Pat. Nos. 5,041,426 and 4,880,784 to Robins et al.

One possible target of immunomodulation involves stimulation or suppression of Th1 and Th2 lymphokines. Type I (Th1) cells produce interleukin 2 (IL-2), tumor necrosis factor (TNFα) and interferon gamma (IFNγ) and they are responsible primarily for cell-mediated immunity such as delayed type hypersensitivity and antiviral immunity. Type 2 (Th2) cells produce interleukins, IL-4, IL-5, IL-6, IL-9, IL-10, and IL-13 and are primarily involved in assisting humoral immune responses such as those seen in response to allergens. See, e.g., Mosmann, *Annu. Rev. Immunol.*, 7, 145–73 (1989). D-guanosine analogs have been shown to elicit various effects on lymphokines IL-1, IL-6, INFα and TNFα (indirectly) in vitro (Goodman, *Int. J. Immunopharmacol,* 10, 579–88 (1988); U.S. Pat. No. 4,746, 651 to Goodman) and in vivo (Smee et al., *Antiviral Res.*, 15, 229 (1991); Smee et al., *Antimicrobial Agents and Chemotherapy,* 33, 1487–92 (1989)). However, the ability of the D-guanosine analogs such as 7-thio-8-oxoguanosine to modulate Type 1 or Type 2 cytokines directly in T cells was ineffective or had not been described.

Moreover, it is known that the oral administration of many purine nucleoside analogs are subject to difficulties arising from poor absorption, poor solubility, or degradation in the digestive tract as a result of acidic or alkaline conditions or the action of enzymes, and/or combinations of these phenomena. Thus there remains a need for purine nucleoside analogs with improved oral availability, tolerability, and administration that are used to modulate aspects of the immune system.

SUMMARY OF THE INVENTION

The present invention has addressed this need by the discovery of 3-β-D-ribofuranosylthiazolo[4,5-d]pyrimidine nucleosides, pharmaceutically acceptable prodrugs, pharmaceutically active metabolites, and pharmaceutically acceptable salts thereof (such compounds, prodrugs, metabolites and salts are collectively referred to as "agents") described below, which are useful as immunomodulators.

In a general aspect, the invention relates to compounds of the Formula I:

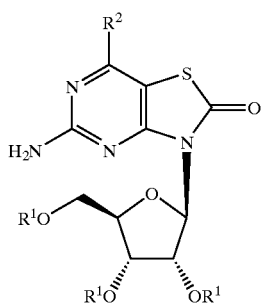

wherein:
  $R^1$ is independently H, $-C(O)R^3$, or a racemic, L-, or D-amino acid group $-C(O)CHNH_2R^4$, wherein $R^3$ is a substituted or unsubstituted alkyl, and $R^4$ is H, or a substituted or unsubstituted alkyl;
  $R^2$ is H, $OR^5$, or $N(R^6)_2$, wherein $R^5$ is independently H or alkyl, and wherein $R^6$ is independently H, substituted or unsubstituted alkyl, cycloalkyl, or together with nitrogen forms a substituted or unsubstituted heterocycloalkyl ring; and
  wherein if $R^2$ is $-OH$, at least one of the $R^1$ groups is a racemic, L-, or D-amino acid group $-C(O)CHNH_2R^4$.

In a preferred embodiment, the invention relates to compounds having Formula I, wherein at least one of the $R^1$ groups is a racemic, L-, or D-amino acid group —C(O)CHNH$_2$R$^4$, wherein R$^4$ is a substituted or unsubstituted alkyl, and wherein the remaining R$^1$ groups are H; R$^2$ is OR$^5$ or N(R$^6$)$_2$, wherein R$^5$ is independently selected from H or alkyl, and wherein R$^6$ is independently H, substituted or unsubstituted alkyl, cycloalkyl, or together with nitrogen forms a substituted or unsubstituted heterocycloalkyl ring.

In another preferred embodiment, the invention relates to compounds having Formula I, wherein at least one of the R$^1$ groups is a L-amino acid group —C(O)CHNH$_2$R$^4$, wherein R$^4$ is a substituted or unsubstituted alkyl, and wherein the remaining R$^1$ groups are H; R$^2$ is OR$^5$ or N(R$^6$)$_2$, wherein R$^4$ is a substituted alkyl, and wherein R$^6$ is independently H or substituted or unsubstituted alkyl.

In yet another preferred embodiment, the invention relates to compounds having Formula I, wherein at least one of the R$^1$ groups is a L-amino acid group —C(O)CHNH$_2$R$^4$, wherein R$^4$ is —CH(CH$_3$)$_2$, and wherein the remaining R$^1$ groups are H; and R$^2$ is OH.

In another aspect of the invention, compounds of the invention are selected from:

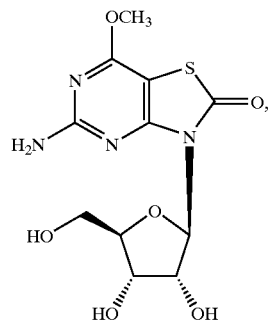
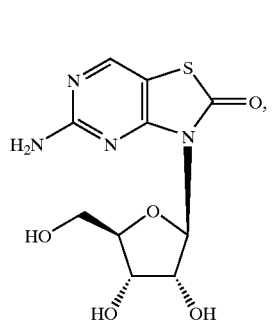
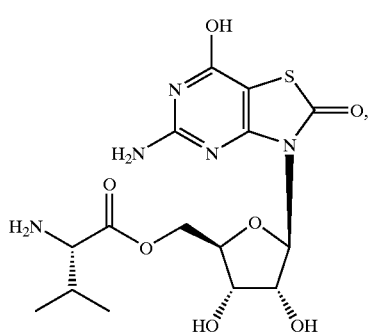
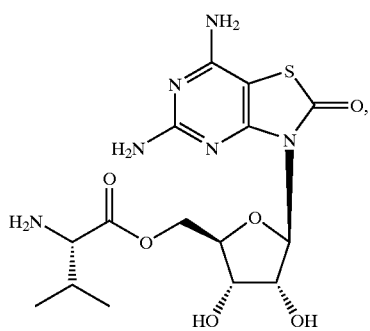
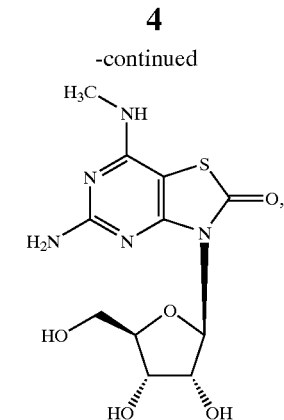
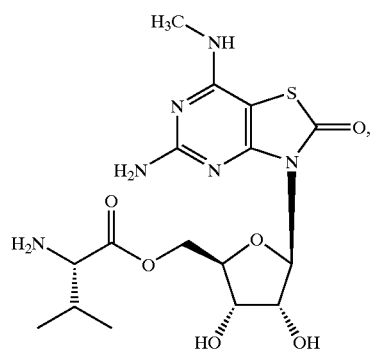
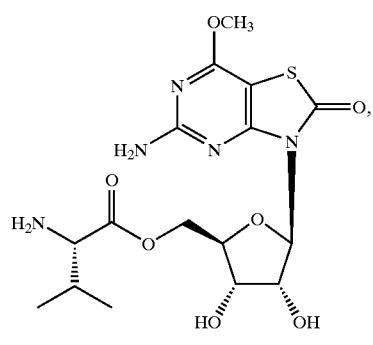
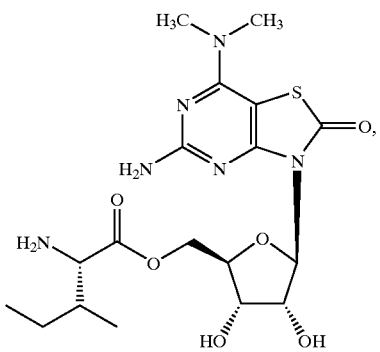

-continued
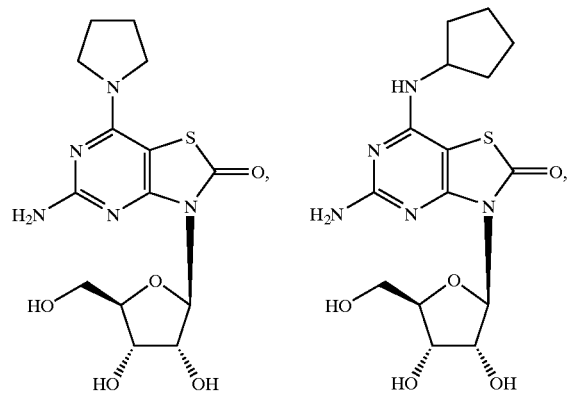
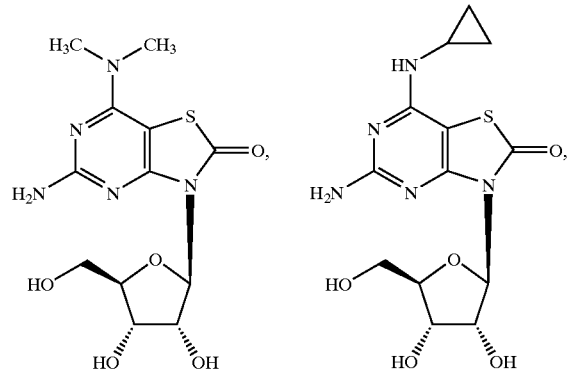
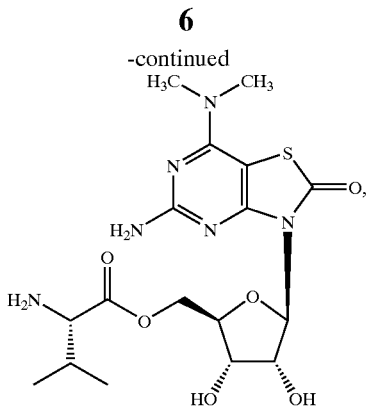
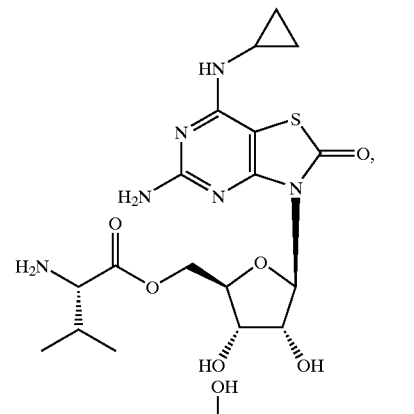
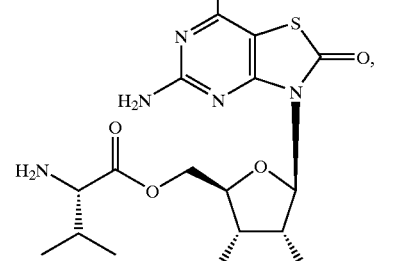
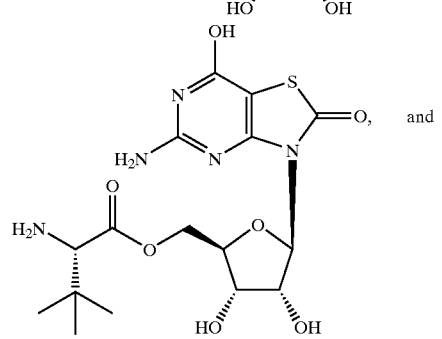
and
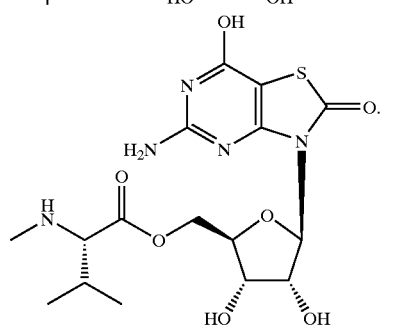

The invention is also directed to pharmaceutically acceptable prodrugs, pharmaceutically active metabolites, and pharmaceutically acceptable salts of the compounds, prodrugs, or metabolites of Formula I. Advantageous methods of making the compounds of Formula I are also described.

The compounds of Formula I are useful as immune system enhancers and have certain immune system properties including modulation, mitogenicity, augmentation, and/ or potentiation or they are intermediates for compounds that have these properties. The compounds are expected to express effects on at least the natural killer, macrophages, and lymphocyte cells of the immune system of a host. Because of these properties they are useful as antiviral and antitumor agents or as intermediates for antiviral and antitumor agents. They can be used to treat an affected host by serving as the active ingredients of suitable pharmaceutical compositions.

In one aspect of the invention, Formula I compounds are utilized to treat the full range of viral diseases in mammals by administering to the mammal a therapeutically effective amount of the compounds. Viral diseases contemplated to be treated with Formula I compounds include acute and chronic infections caused by both RNA and DNA viruses. Without limiting in any way the range of viral infections that may be treated, compounds of Formula I are particularly useful in the treatment of infections caused by adenovirus, cytomegalovirus, hepatitis A virus (HAV), hepatitis B virus (HBV), flaviviruses including Yellow Fever virus and hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, poliovirus, poxvirus (including smallpox and monkeypox virus), rhinovirus, respiratory syncytial virus (RSV), multiple families of viruses that cause hemorrhagic fevers, including the Arenaviruses (LCM, Junin virus, Machup virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, and tickborne viruses such as Crimean-Congo Hemorrhagic fever virus.

In another aspect of the invention, Formula I compounds are utilized to treat bacterial, fungal, and protozoal infections in mammals by administering to the mammal a therapeutically effective amount of the compounds. The full range of pathogenic microorganisms is contemplated to be treatable by the compounds of the present invention, including without limitation those organisms that are resistant to antibiotics. The ability of Formula I compounds to activate multiple components of the immune system bypasses resistance mechanisms commonly found to reduce susceptibility to antibiotics, and thus treatment of infections in a mammal caused by such resistant microorganisms by Formula I compounds is a particular utility of the present invention.

In another aspect of the invention, Formula I compounds are utilized to treat tumors in mammals by administering to the mammal a therapeutically effective amount of the compounds. Tumors or cancers contemplated to be treated include those caused by virus, and the effect may involve inhibiting the transformation of virus-infected cells to a neoplastic state, inhibiting the spread of viruses from transformed cells to other normal cells, and/or arresting the growth of virus-transformed cells. The compounds of Formula I are expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemias.

In another aspect of the invention, a method of treating a mammal comprises administering a therapeutically and/or prophylactically effective amount of a pharmaceutical containing a compound of the invention. In this aspect the effect may relate to modulation of some portion of the mammal's immune system, especially modulation of cytokine activities of Th1 and Th2, including but not restricted to the interleukin family, e.g., IL-1 through IL-12, and other cytokines such as TNF alpha, and interferons including interferon alpha, interferon theta, and interferon gamma, and their downstream effectors. Where modulation of Th1 and Th2 cytokines occurs, it is contemplated that the modulation may include stimulation of both Th1 and Th2, suppression of both Th1 and Th2, stimulation of either Th1 or Th2, and suppression of the other, or a bimodal modulation in which one effect on Th1 /Th2 levels (such as generalized suppression) occurs at a high concentration, while another effect (such as stimulation of either Th1 or Th2 and suppression of the other) occurs at a lower concentration.

In another aspect of the invention, pharmaceutical compositions containing a compound of Formula I are administered in a therapeutically effective dose to a mammal that is receiving anti-infective drugs not included in Formula I. In a preferred aspect of this invention, the pharmaceutical compositions containing a compound of Formula I are administered in a therapeutically effective dose with anti-infective drug(s) that act directly upon the infectious agent to inhibit the growth of or kill the infectious agent.

In a preferred aspect of the invention, a pharmaceutical composition comprising a therapeutically effective amount of a compound according to Formula I provides for improved oral availability and administration as an immunomodulator. In another preferred aspect of the invention, a pharmaceutical composition comprising a therapeutically effective amount of a compound according to Formula I provides for masking the active structure as the agent passes through lymphoid tissue lining the stomach, thereby minimizing activation of this tissue and allowing for improved oral tolerability.

DETAILED DESCRIPTION OF THE INVENTION AND PREFERRED EMBODIMENTS

Figure 1:
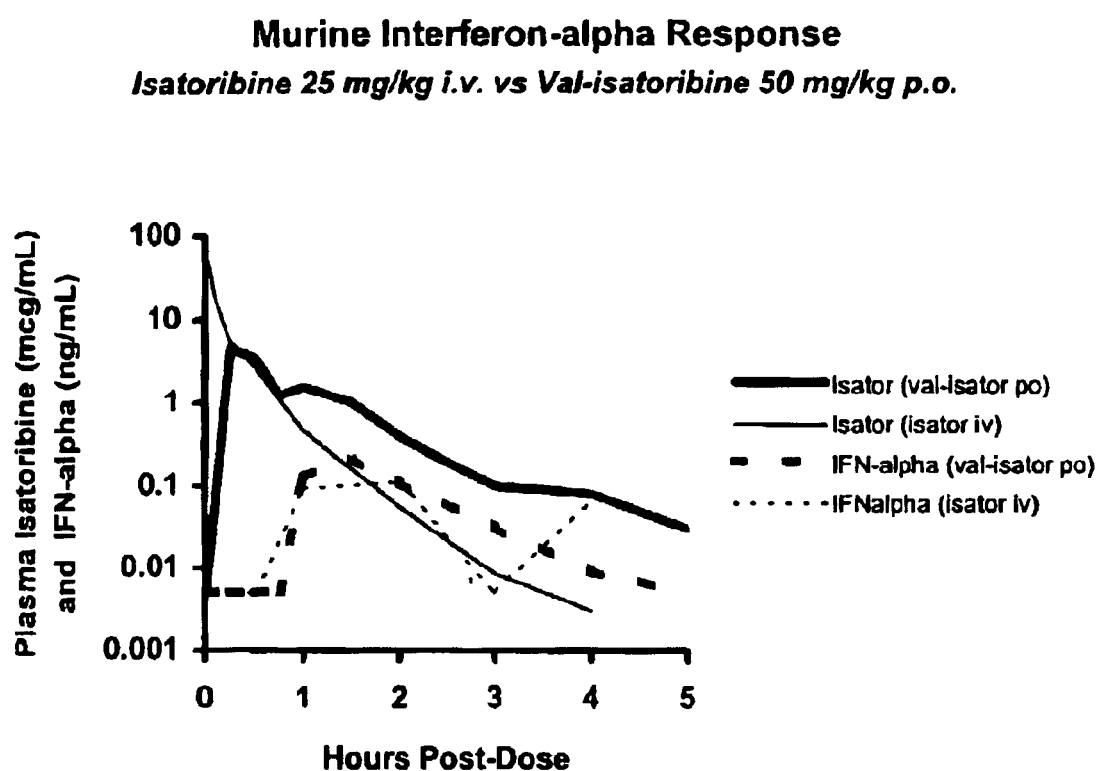
FIG. 1 is a graphical depiction of plasma levels of isatoribine and interferon alpha in mice.

Where the following terms are used in this specification, they are used as defined below:

The terms "comprising" and "including" are used herein in their open, non-limiting sense.

The term "nucleoside" refers to a compound composed of any pentose or modified pentose moiety attached to a specific position of a heterocycle or to the natural position of a purine (9-position) or pyrimidine (1-position) or to the equivalent position in an analog.

The term "purine" refers to nitrogenous bicyclic heterocycles.

The term "pyrimidine" refers to nitrogenous monocyclic heterocycles.

The term "D-nucleosides" refers to the nucleoside compounds that have a D-ribose sugar moiety (e.g., Adenosine).

The term "L-nucleosides" refers to the nucleoside compounds that have a L-ribose sugar moiety.

The term "alkyl" as used herein refers to a straight- or branched-chain alkyl group having one to twelve carbon atoms. Exemplary alkyl groups include methyl (Me, which also may be structurally depicted by "/"), ethyl (Et), n-propyl, isopropyl, butyl, isobutyl, sec-butyl, tert-butyl (tBu), pentyl, isopentyl, tert-pentyl, hexyl, isohexyl, and the like.

The term "alkoxy" refers to —O-alkyl. Illustrative examples include methoxy, ethoxy, propoxy, and the like.

The term "halogen" represents chlorine, fluorine, bromine or iodine. The term "halo" represents chloro, fluoro, bromo or iodo.

The term "cycloalkyl" refers to a saturated or partially saturated, monocyclic or fused or spiro polycyclic, carbocycle having from three to twelve ring atoms per ring. Illustrative examples of cycloalkyl groups include the following moieties:

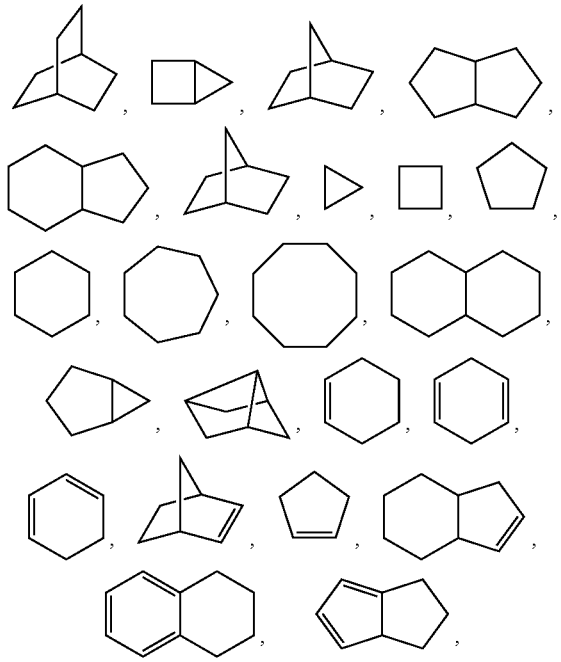

and the like.

A "heterocycloalkyl" refers to a monocyclic, or fused or spiro polycyclic, ring structure that is saturated or partially saturated and has from three to twelve ring atoms per ring selected from C atoms and N, O, and S heteroatoms. Illustrative examples of heterocycloalkyl groups include:

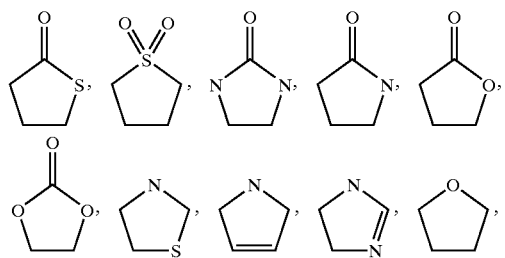

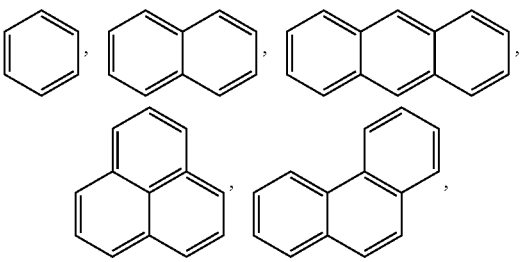

and the like.

The term "aryl" (Ar) refers to a monocyclic, or fused or spiro polycyclic, aromatic carbocycle (ring structure having ring atoms that are all carbon) having from three to twelve ring atoms per ring. Illustrative examples of aryl groups include the following moieties:

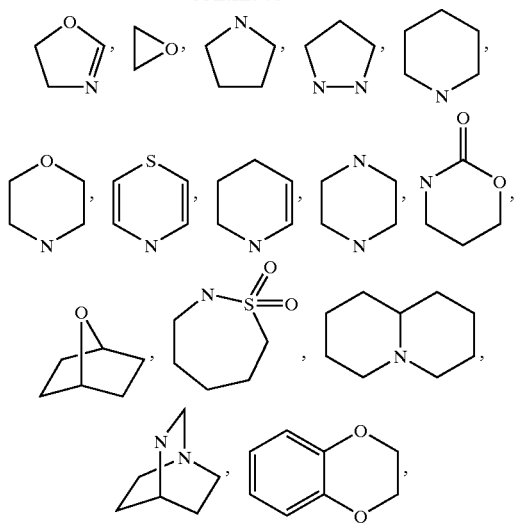

and the like.

The term "substituted" means that the specified group or moiety bears one or more substituents. The term "unsubstituted" means that the specified group bears no substituents. A substituted alkyl, cycloalkyl, or heterocycloalkyl is substituted by one or more substituents including halogen (F, Cl, Br, or I), lower alkyl ($C_{1-6}$), —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and (iii) relieving the disease, disorder, or condition, i.e., causing regression of the disease, disorder, and/or condition.

The terms "α" and "β" indicate the specific stereochemical configuration of a substituent at an asymmetric carbon atom in a chemical structure as drawn. The compounds described herein are all in the D-furanosyl configuration.

The compounds of the invention may exhibit the phenomenon of tautomerism. While Formula I cannot expressly depict all possible tautomeric forms, it is to be understood that Formula I is intended to represent any tautomeric form of the depicted compound and are not to be limited merely to a specific compound form depicted by the formula drawings. For example, it is understood for Formula I that regardless of whether or not the substituents are shown in their enol or their keto form, they represent the same compound (as shown in the example below).

solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172–178, 949–982 (1995). See also Bertolini et al., *J. Med. Chem.*, 40, 2011–2016 (1997); Shan, et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); Larsen, *Design and Application of*

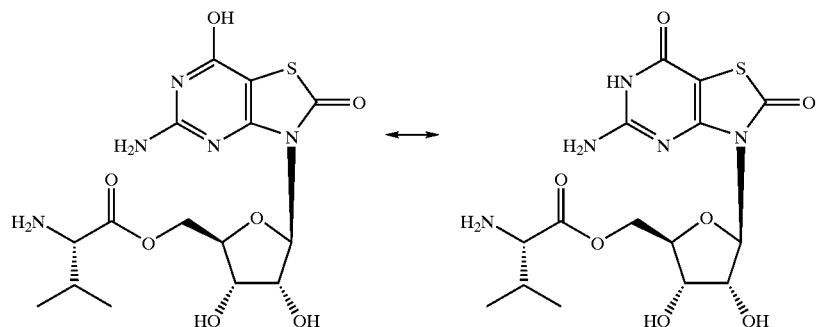

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by

*Prodrugs*, Drug Design and Development (Krogsgaard-Larsen et al., eds., Harwood Academic Publishers, 1991); Dear et al., *J. Chromatogr. B*, 748, 281–293 (2000); Spraul et al., *J. Pharmaceutical & Biomedical Analysis*, 10, 601–605 (1992); and Prox et al., *Xenobiol.*, 3, 103–112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid , such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

A further aspect of the present invention is directed to a pharmaceutical composition comprising a pharmaceutically acceptable carrier or a diluent and a therapeutically effective amount of a Formula I compound, a pharmaceutically acceptable salt, hydrate, ester, solvate, prodrug, metabolite, or stereoisomer.

Formula I compounds are useful in the manufacture of pharmaceutical formulations comprising an effective amount thereof in conjunction with or as an admixture with excipients or carriers suitable for either enteral or parenteral application. As such, formulations of the present invention suitable for oral administration may be in the form of discrete units such as capsules, cachets, tablets, troche or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The composition will usually be formulated into a unit dosage form, such as a tablet, capsule, aqueous suspension or solution. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

Particularly preferred formulations include tablets and gelatin capsules comprising the active ingredient together with (a) diluents, such as lactose, dextrose, sucrose, mannitol, sorbitol, cellulose, dried corn starch, and glycine; and/or (b) lubricants, such as silica, talcum, stearic acid, its magnesium or calcium salt, and polyethylene glycol.

Tablets may also contain binders, such as magnesium aluminum silicate, starch paste, gelatin, tragacanth, methylcellulose, sodium carbosymethylcellulose and polyvinylpyrrolidone; carriers, such as lactose and corn starch; disintegrants, such as starches, agar, alginic acid or its sodium salt, and effervescent mixtures; and/or absorbents, colorants, flavors, and sweeteners. The compositions of the invention may be sterilized and/or contain adjuvants, such as preserving, stabilizing, swelling or emulsifying agents, solution promoters, salts for regulating osmotic pressure, and/or buffers. In addition, the composition may also contain other therapeutically valuable substances. Aqueous suspensions may contain emulsifying and suspending agents combined with the active ingredient. All oral dosage forms may further contain sweetening and/or flavoring and/or coloring agents.

These compositions are prepared according to conventional mixing, granulating, or coating methods, respectively, and contain about 0.1 to 75% of the active ingredient, preferably about 1 to 50% of the same. A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

When administered parenterally, the composition will normally be in a unit dosage, sterile injectable form (aqueous isotonic solution, suspension, or emulsion) with a pharmaceutically acceptable carrier. Such carriers are preferably non-toxic, parenterally-acceptable and contain non-therapeutic diluents or solvents. Examples of such carriers include water; aqueous solutions, such as saline (isotonic sodium chloride solution), Ringer's solution, dextrose solution, and Hanks' solution; and nonaqueous carriers, such as 1,3-butanediol, fixed oils (e.g., corn, cottonseed, peanut, sesame oil, and synthetic mono- or di-glyceride), ethyl oleate, and isopropyl myristate.

Oleaginous suspensions can be formulated according to techniques known in the art using suitable dispersing or wetting agents and suspending agents. Among the acceptable solvents or suspending mediums are sterile fixed oils. For this purpose, any bland fixed oil may be used. Fatty acids, such as oleic acid and its glyceride derivatives, including olive oil and castor oil, especially in their polyoxyethylated forms, are also useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound. Common excipients include cocoa butter, beeswax and polyethylene glycols or other fatty emulsions or suspensions.

Formulations suitable for nasal or buccal administration (such as self-propelling powder dispensing formulations), may comprise about 0.1% to about 5% w/w of the active ingredient or, for example, about 1% w/w of the same. In addition, some formulations can be compounded into a sublingual troche or lozenge.

Moreover, the compounds may be administered topically, especially when the conditions addressed for treatment involve areas or organs readily accessible by topical application, including disorders of the eye, the skin or the lower intestinal tract.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The formulations may conveniently be presented in unit dosage form and may be prepared by any of the methods well known in the art of pharmacy. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

The pharmaceutical composition of the present invention is used in amount that arc therapeutically effective and the amounts used may depend upon the desire release profile, the concentration of the pharmaceutical composition required for the sensitizing effect, and the length of time that the pharmaceutical composition has to be released for treatment.

The Formula I compounds of the invention are preferably administered as a capsule or tablet containing a single or divided dose of the compound, or as a sterile solution, suspension, or emulsion, for parenteral administration in a single or divided dose.

The compounds of the invention are used in the composition in amounts that are therapeutically effective. While the effective amount of the Formula I compounds will depend upon the particular compound being used, amounts of these compounds varying from about 1% to about 65% have been easily incorporated into liquid or solid carrier delivery systems.

For medical use, the amount required of a Formula I compound to achieve a therapeutic effect will vary according to the particular compound administered, the route of administration, the mammal under treatment, and the particular disorder in disease concerned. A suitable systemic dose of a Formula I compound for a mammal suffering from, or likely to suffer from, any condition as described herein is typically in the range of about 0.1 to about 100 mg of base per kilogram of body weight. It is understood that the ordinarily skilled physician or veterinarian will readily be able to determine and prescribe the amount of the compound effective for the desired prophylactic or therapeutic treatment.

In so proceeding, the physician or veterinarian may employ an intravenous bolus followed by an intravenous infusion and repeated administrations, as considered appropriate. In the methods of the present invention, the compounds may be administered, for example, orally, parentally, in inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

Parenteral includes, but is not limited to, the following examples of administration: intravenous, subcutaneous, intramuscular, intraspinal, intraosseous, intraperitoneal, intrathecal, intraventricular, intrasternal or intracranial injection and infusion techniques, such as by subdural pump. Invasive techniques are preferred, particularly direct administration to damaged neuronal tissue. While it is possible for the Formula I compound(s) to be administered alone, it is preferable to provide it as part of a pharmaceutical formulation.

To be effective therapeutically as central nervous system targets, the compounds used in the methods of the present invention should readily penetrate the blood-brain barrier when peripherally administered. Compounds that cannot penetrate the blood-brain barrier, however, can still be effectively administered by an intraventricular route.

The compounds used in the methods of the present invention may be administered by a single dose, multiple discrete doses or continuous infusion. Since the compounds are small, easily diffusible and relatively stable, they are well suited to continuous infusion. Pump means, particularly subcutaneous or subdural pump means, are preferred for continuous infusion.

For the methods of the present invention, any effective administration regimen regulating the timing and sequence of doses may be used. Doses of the compounds preferably include pharmaceutical dosage units comprising an efficacious quantity of active compound. By an efficacious quantity is meant a quantity sufficient to provide immune enhancing response and/or derive the desired beneficial effects through administration of one or more of the pharmaceutical dosage units.

An exemplary daily dosage unit for a vertebrate host comprises an amount of from about 0.001 mg/kg to about 50 mg/kg. Typically, dosage levels on the order of about 0.1 mg to about 10,000 mg of the active ingredient compound are useful in the treatment of the above conditions, with preferred levels being about 0.5 mg to about 2,000 mg. The specific dose level for any particular patient will vary depending upon a variety of factors, including the activity of the specific compound employed; the age, body weight, general health, sex, and diet of the patient; the time of administration; the rate of excretion, any combination of the compound with other drugs; the severity of the particular disease being treated; and the form and route of administration. Typically, in vitro dosage-effect results provide useful guidance on the proper doses for patient administration. Studies in animal models can also be helpful. The considerations for determining the proper dose levels are well known in the art.

The compounds and compositions can be co-administered with one or more therapeutic agents either (i) together in a single formation, or (ii) separately in individual formulations designed for optimal release rates of their respective active agent. Each formulation may contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the invention are administered in combination with one or more other therapeutic agents, specific dose levels for those agents will depend upon considerations such as those identified above for compositions and methods of the invention in general.

For the methods of the present invention, any administration regimen regulating the timing and sequence of delivery of the compound can be used and repeated as necessary to effect treatment. Such regimen may include pretreatment and/or co-administration with additional therapeutic agents.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylformamide (DMF) were purchased from Aldrich in Sure Seal bottles and used as received. Unless otherwise indicated, the following solvents and reagents were distilled under a blanket of dry nitrogen. THF, and $Et_2O$ were distilled from Na-benzophenone ketyl; $CH_2Cl_2$, diisopropylamine, pyridine and $Et_3N$ were distilled from $CaH_2$; MeCN was distilled first from $P_2O_5$, then from $CaH_2$; MeOH was distilled from Mg; PhMe, EtOAc and i-PrOAc were distilled from $CaH_2$; TFAA was purified via simple atmospheric distillation under dry argon.

The reactions set forth below were done generally under a positive pressure of argon at an ambient temperature (unless otherwise stated) in anhydrous solvents, and the reaction flasks were fitted with rubber septa for the introduction of substrates and reagents via syringe. Glassware was oven dried and/or heat dried. The reactions were assayed by TLC and terminated as judged by the consumption of starting material. Analytical thin layer chromatography (TLC) was performed on aluminum-backed silica gel 60 $F_{254}$ 0.2 mm plates (EM Science), and visualized with UV light (254 nm) followed by heating with commercial ethanolic phosphomolybdic acid. Preparative thin layer chromatography (TLC) was performed on aluminum-backed silica gel 60 $F_{254}$ 1.0 mm plates (EM Science) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230–400 mesh silica gel or 50–200 mesh neutral alumina.

Hydrogenolysis was done at the pressure indicated in the examples or at ambient pressure.

$^1$H-NMR spectra were recorded on a Varian Mercury-VX400 instrument operating at 400 MHz and $^{13}$C-NMR spectra were recorded operating at 75 MHz. NMR spectra were obtained as $CDCl_3$ solutions (reported in ppm), using chloroform as the reference standard (7.27 ppm and 77.00 ppm), $CD_3OD$ (3.4 and 4.8 ppm and 49.3 ppm), DMSO-$d_6$, or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Infrared (IR) spectra were recorded on a FT-IR Spectrometer as neat oils, as KBr pellets, or as $CDCl_3$ solutions, and when given are reported in wave numbers (cm $^{-1}$). Mass spectra reported are (+)-ES LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures utilize many common chemical abbreviations, THF (tetrahydrofuran), DMF (N,N-dimethylformamide), EtOAc (ethyl acetate), DMSO (di-methyl sulfoxide), DMAP (4-dimethylaminopyridine), DBU (1,8-diazacyclo[5.4.0] undec-7-ene), DCM (4-(dicyanomethylene)-2-methyl-6-(4-dimethylamino-styryl)-4H-pyran), MCPBA (3-chloroperoxybenzoic acid), EDC (1-(3-dimethylaminopropyl)-3-ethylcarbodiimide hydrochloride), HATU (O-(7-azabenzotriazol-1-yl)-1,1,3,3-tetramethyluronium hexafluorophosphate), HOBT (1-hydroxybenzotriazole hydrate), TFAA (trifluoroacetic anhydride), pyBOP (benzotriazol-1-yloxy) tripyrrolidinophosphonium hexafluorophosphate), DIEA (diisopropylethylamine), and the like.

Scheme 1 shows a general procedure to prepare the 5'-amino acid esters of 5-amino-3-β-D-ribofuranosylthiazolo[4,5-d]pyrimidine-2,7-dione.

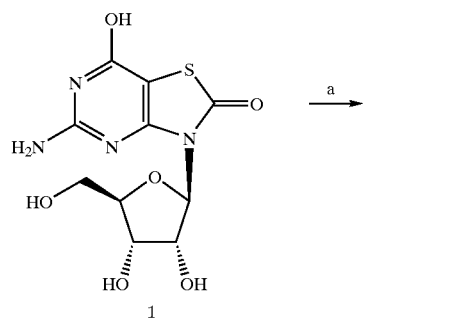

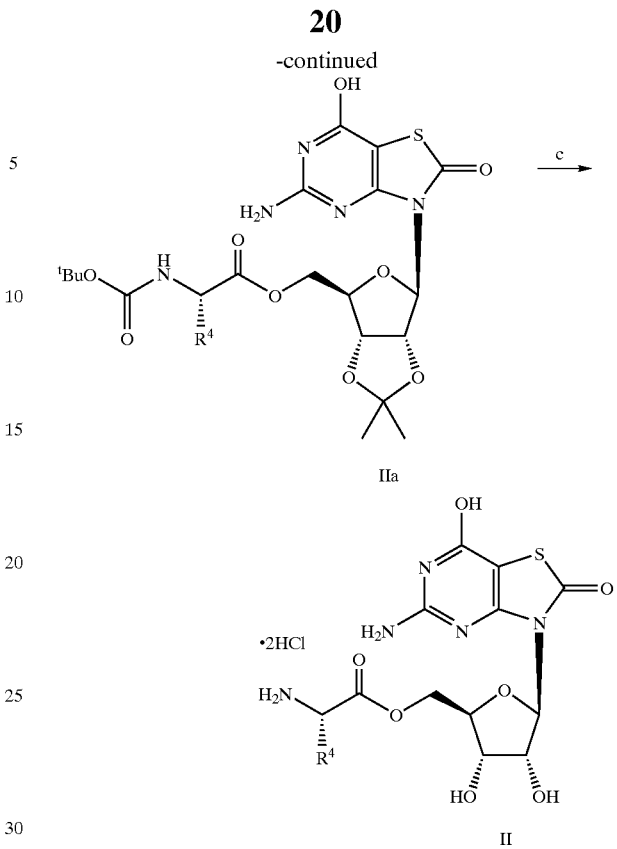

a) 2,2-dimethoxypropane, acetone, DMSO, $MeSO_3H$, 0° C.
b) BOC-NHCHR$^4$CO$_2$H, EDC, DMAP, PhMe, 0° C. - rt
c) anh. HCl, iPrOAc, iPrOH In a typical synthetic route, the 2',3'-hydroxyl groups of the β-D-ribose moiety of 5-amino-3-β-D-ribofuranosylthiazolo[4,5-d]pyrimidine-2,7-dione is first protected, preferably with an acetonide as shown in 2. The free 5'-hydroxyl can then be subjected to a variety of esterification methods with a N-protected amino acid to form IIa. The nitrogen of the amino acid ester and the 2',3'-hydroxyls of the ribose unit are then subjected to various deprotection conditions, preferably concurrently, followed by salt formation of the free amine of the amino acid ester as illustrated for II.

EXAMPLE 1

5-Amino-3-(5'-O-L-valinyl-β-D-ribofuranosyl) thiazolo[4,5-d]pyrimidine-2,7-dione Dihydrochloride (3)

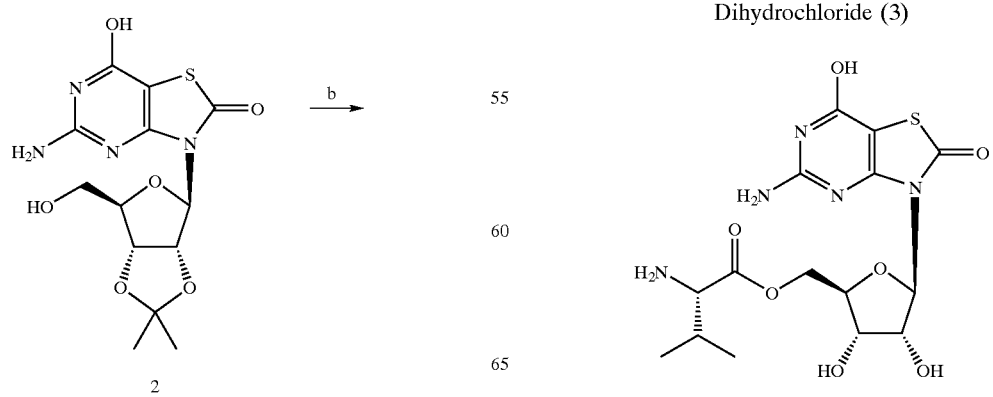

Step 1: Preparation of 5-Amino-3-(2',3'-O-isopropylidene-β-D-ribofuranosyl) thiazolo[4,5-d]pyrimidine-2,7-dione To a heterogeneous mixture of 1 (5.37 g, 17.0 mmol, prepared according to the procedure given in U.S. Pat. No. 5,041,426 (Example 2), which is incorporated by reference in its entirety) in acetone (40 mL) contained in a 250 mL Morton flask was added successively 2,2-DMP (6.26 mL, 50.9 mmol), DMSO (6.6 mL), and MeSO$_3$H (220 µL, 3.39 mmol) at room temperature. The reaction mixture was stirred vigorously, becoming homogeneous and golden yellow as the diol was consumed. TLC analysis (SiO$_2$, 10% MeOH—CHCl$_3$) indicated reaction completion after 6 h. Undissolved solids were removed via gravity filtration using fluted Whatman type 1 filter paper. This was followed by pouring of the filtrate into 10 volumes of ice water (~400 mL), resulting in immediate precipitation of a white solid. After a brief period of stirring, NaHCO$_3$ (285 mg, 3.39 mmol) dissolved in water (10 mL) was added to neutralize the MeSO$_3$H. Vigorous stirring in the Morton reactor was continued for 15 min, whereupon the mixture was filtered through a coarse scintered glass funnel. The solid material was washed with ice water (100 mL), air dried, then dried further under high vacuum at 65° C., affording 5.36 g (88%) of the acetonide 2 as a white solid: mp 280–81° C.; $^1$H (DMSO-d$_6$) δ 1.28 (s, 3H), 1.47 (s, 3H), 3.43–3.55 (m, 2H), 3.95–3.99 (m, 1H), 4.77–4.80 (m, 1H), 4.88–4.91 (m, 1H), 5.24-5.26 (m, 1H), 5.99 (s, 1H), 6.97 (br s, 2h), 11.25 (s, 1H).

Step 2: Preparation of 5-Amino-3-(2',3'-O-isopropylidene-5'-N-tert-butoxycarbonyl-L-valinyl)-β-D-ribifuranosyl)-thiazolo[4,5-d]pyrimidine-2,7-dione (4)

To a solution of N-butoxycarbonyl-(L)-valine (671 mg, 2.81 mmol) in THF (9 mL) at 0° C. was added EDC (588 mg, 3.07 mmol). The resultant homogeneous mixture was stirred 45 min at 0° C., at which point it had become heterogeneous, and solid acetonide 2 from Step 1 above (1.00 g, 2.81 mmol) was added as one portion. Subsequently added was solid DMAP (522 mg, 4.27 mmol). The reaction mixture was permitted to reach room temperature, and stirred an additional 5 h, whereupon it was concentrated at 25° C. via rotary evaporation to a yellow syrup. The residue was dissolved in EtOAc (50 mL), partitioned with 1 N HCl (10 mL) followed by neutralization of acid with saturated aqueous NaHCO$_3$ (10 mL). The acidic aqueous phase was further extracted with EtOAc (2×50 mL), and then partitioned with the basic aqueous phase. The combined organic phases were dried over Na$_2$SO$_4$, filtered through a short pad of SiO$_2$, and concentrated, affording 1.480 g (96%) of Boc-protected amino acid ester 4 as a foam: mp 158° C. (dec); $^1$H (CDCl$_3$) δ 0.86 (d, J=7.0, 3H), 0.95 (d, J =7.0 3H), 1.35 (s, 3H), 1.44 (s, 9H), 1.56 (s, 3H), 1.75 (br s, 1H), 2.08–2.19 (m, 1H), 4.20–4.24 (m, 2H), 4.30–4.37 (m, 1H), 4.56 (dd, J=11.0, 5.9, 1H), 4.96 (dd, J=6.2, 3.7, 1H), 5.11 (br d, J=8.8, 1H), 5.29 (br d, J=6.6, 1H), 5.88 (br s, 2H), 6.23 (s, 1H).

Step 3: Preparation of 5-Amino-3-(5'-O-L-valinyl-β-D-ribofuranosyl)thiazolo[4,5-d]pyrimidine-2,7-dione Dihydrochloride (3)

A stream of HCl gas was passed through a bubbler of concentrated H$_2$SO$_4$, and subsequently directed (via fritted dispersion tube) into a 250 mL 3-neck Morton flask containing dry isopropyl acetate (80 mL) at 0° C. until a saturated solution was obtained. To this was added a solution of the Boc-amino acid ester from Step 2 above (5.53 g, 9.95 mmol) in isopropyl acetate (30 mL), resulting in the formation of a white solid precipitate within 5 min. To this was added 10% (v/v) IPA (11 mL). The reaction mixture was warmed to room temperature, then stirred 12 h. The heterogeneous reaction mixture was diluted with dry toluene (100 mL). Filtration using a medium pore scintered glass funnel under N$_2$ provided an off-white, amorphous solid. Trituration of the solid in dry THF was followed by filtration and vacuum drying at 65° C., affording 3.677 g (81%) of the title compound 3 as a white solid: mp 166–68° C. (dec); $^1$H (DMSO-d$_6$) δ 0.90 (d, J=7.0, 3H), 0.94 (d, J=7.0, 3H), 2.14–2.18 (m, 1H). 3.83–3.85 (m, 1H), 3.96–4.00 (m, 1H), 4.23–4.28 (m, 2H), 4.42 (dd, J=11.7, 3.4, 1H). 4.75 (dd, J=10.3, 5.5, 1H), 5.81 (d, J=4.4, 1H), 6.46 (br s, 3H), 7.23 (br s, 2H), 8.47 (s, 3H), 11.5 (br s, 1H).

Elemental analysis for C$_{15}$H$_{21}$N$_5$O$_7$S.2HCl: calc'd: C, 36.89; H, 4.75; Cl, 14.52; N, 14.34; S, 6.57; found: C, 37.03: H, 4.74; Cl, 14.26; N, 14.24; S, 6.42.

EXAMPLE 2

5-Amino-3-(5'-O-L-isoleucyl-β-D-ribofuranosyl) thiazolo[4,5-d]pyrimidine-2,7-dione 3/2 Hydrochloride (5)

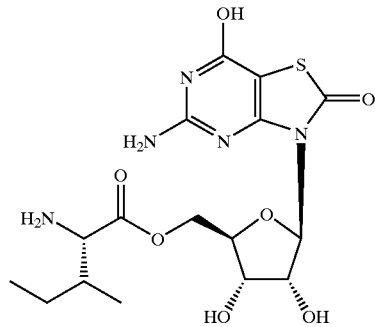

Step 1: Preparation of 5-Amino-3-(2',3'-O-isopropylidene-5'-N-tert butoxycarbonyl-L-isoleucyl)-β-D-ribofuranosyl)-thiazolo[4,5-d]pyrimidinine-2,7-dione (6)

In a manner similar to step 2 of Example 1, 5-Amino-3-(2',3'-O-isopropylidene-5'-N-tert-butoxycarbonyyl-L-isoleucyl)-β-D-ribofuranosyl)-thiazolo[4,5-d]pyrimidine-2,7dione 6 was prepared in a yield of 93% from 5-Amino-3-(2',3'-O-isopropylidene-β-D-ribofuranosyl)-thiazolo[4,5-d]pyrimidine-2,7-dione 2 and N-tert-butoxy-L-isoeucine 7 as an off-white foam: $^1$H NMR (400 MHz, d$_6$-DMSO) δ 11.29 (s, 1H), 7.09 (d, J=8.0, 1H), 7.02 (br s, 1H), 6.02 (s, 1H), 5.28 (d, J=6.2, 1H), 5.06 (br s, 1H), 4.16–4.22 (m, 2H), 3.85 (dd, J=8.0, 6.6, 1H), 1.68 (br s, 1H), 1.47 (s, 3H), 1.34 (s, 9H), 1.29 (s, 3H), 0.71–0.89 (m, 5H).

Step 2: Preparation of 5-Amino-3-(5'-O-L-isoleucyl-β-D-ribofuranosyl)thiazolo-[4,5-d]pyrimidine-2,7dione Diydrochloride (5)

In a manner similar to Step 3 of Example 2 was prepared the title compound as a white solid from the above intermediate in an 80% yield: mp 173–174° C. (dec); $^1$H NMR (400 MHz, d$_6$-DMSO) δ 11.41 (br s, 1H), 8.41 (br s, 3H), 7.15 (br s, 2H), 5.82 (d, J=4.8, 1H), 4.50–5.00 (m, 2H), 4.40

(dd, J=11.7, 3.3, 1H), 4.21–4.30 (m, 2H), 3.91 4.0 (m, 2H), 1.84–1.91 (m, 1H), 1.37–1.44 (m, 1H), 1.19–1.27 (m, 1H), 0.80–0.87 (m, 6H). Elemental analysis for $C_{16}H_{23}N_5O_7S.3/2HCl$: calc'd: C, 39.69; H, 5.10; N, 14.47; Cl, 10.98; S, 6.62; found: C, 39.05; H, 5.13; N, 13.73; Cl, 11.08; S, 6.02.

EXAMPLE 3

5-Amino-3-(5'-O-[α-L-tert-butylglycinyl]-β-D-ribofuranosyl)thiazolo[4,5-d]pyrimidine-2,7-dione Hydrochloride (8)

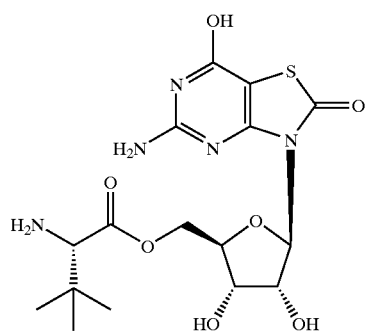

Step 1: Preparation of 5-Amino-3-(2',3'-O-isopropylidene-5'-N-tert-butoxycarbonyl-[α-L-tert-butylglycyl]-β-D-ribofuranosyl)-thianosyl)-thiozolo[4,5-d]pyrimidine-2,7-dione (9)

In a manner similar to Step 2 of Example 1, 5-Amino-3-(2',3'-O-isopropylidene-5'-N-tert-butoxycarbonyl-[α-L-butyglycinyl]-β-D-ribofuranosyl)-thiazolo[4,5-d]pyrimidine-2,7-dione 10 was prepared in a yield of 66% from 5-Amino-3-(2,3-O-isopropylidene-β-D-ribofuranosyl)-thiazolo[4,5-d]pyrimidinone-2,7dione 2 and N-α-L-tert-butoxyglycine as an off-white foam: $^1$H NMR (400 MHz, d$_6$-DMSO) δ 11.28 (br s, 1H), 6.70–7.40 (m, 3H), 6.02 (s, 1H), 5.30 (d, J=6.2, 1H), 5.05 (br s, 1H), 4.17–4.24 (m, 3H), 3.77 (d, J=8.4, 1H), 1.47 (s, 3H), 1.33 (s, 9H), 1.29 (s, 3H), 0.85 (s, 9H).

Step 2: Preparation of 5-Amino-3-(5'-O-[α-L-tert-butylglycyl]-β-D-ribofuranosyl)-thiazolo[4,5-d]pyrimidine-2.7-dione (8)

In a manner similar to Step 3 of Example 1 was prepared the title compound 8 as a white solid from the above intermediate in an 80% yield: mp 202–203° C. (dec); $^1$H NMR (400 MHz, d$_6$-DMSO) δ 11.35 (br s, 1H), 8.31 (br s, 3H), 7.08 (br s, 2H), 5.83 (d, J=4.0, 1H), 5.45 (br s, 1H), 5.21 (br s, 1H), 4.77–4.82 (m, 1H), 4.42 (dd, J=11.4 2.6, 1H), 4.23–4.28 (m, 1H), 3.96–4.04 (m, 1H), 3.74 (s, 1H), 0.97 (s, 9H). Elemental analysis for $C_{16}H_{23}N_5O_7S$ o HCl: calc'd: C, 41.25; H, 5.19; N, 15.03; Cl, 7.61; S, 6.88; found: C, 40.41; H, 5.41; N, 14.16; Cl, 7.01; S, 6.23.

EXAMPLE 4

5-Amino-3-(5'-O-[α-L-N-methylvalinyl]-β-D-ribofuranosyl)thiazolo[4,5-d]pyrimidine-2,7-dione Hydrochloride (11)

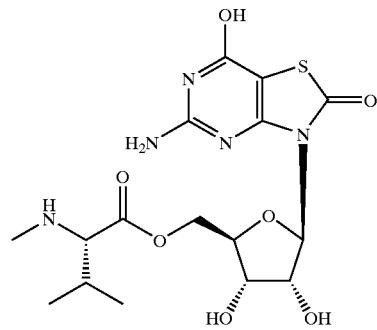

Step 1: Preparation of 5-Amino-3-(2',3'-O-isopropylidene-5'-N-tert-butoxycarbonyl-[α-L-N-methylvalinyl]-β-D-ribofuranosyl)-thiazolo[4,5-d]pyrimidine-2,7-dione (12)

In a manner similar to Step 2 of Example 1, 5-Amino-3-(2',3'-O-isopropylidene-5'-N-tert-butoxycarbonyl-[α-L-N-methylvalinyl]-β-D-ribofuranosyl)-thiazolo[4,5-d]pyrimidine-2,7-dione 12 was prepared in a yield of 63% from 5-Amino-3-(2',3'-O-isopropylidene-β-D-ribofuranosyl)-thiazolo[4,5-d]pyrimidine-2,7dione 2 and N-tert-butoxy-L-N-methylvaline 13 as an off-white foam: $^1$H NMR (400 MHz, d$_6$-DMSO) rotameric carbamate δ 11.28 (br s, 1H), 7.00 (br s, 2H), 6.02 (s, 1H), 5.27 (d, J J=6.6, 1H), 5.04 (br s, 1H), 4.14–4.28 (m, 3H), 3.91 (d, J=9.5, 1H), 2.79 (br s, 3H), 2.09 (br s, 1H), 1.46 (s, 3H), 1.36 (s, 4.5H), 1.32 (s, 4.5H), 1.28 (s, 3H), 0.78–0.89 (m, 6H).

Step 2: 5-Amino-3-(5'-O-[α-L-N-methylvalinyl]-β-D-ribofuranosyl)thiazolo[4,5-d]pyrimidine-2,7-dione Hydrochloride (11)

In a manner similar to Step 3 of Example 1 was prepared the title compound 11 as a slightly impure white solid from the above intermediate in an 60% yield: mp>180° C. (dec); $^1$H NMR (400 MHz, d$_6$-DMSO) δ 11.31 (br s, 1H), 9.05 (br s, 2H), 7.05 (br s, 2H), 5.83 (d, J=4.4, 1H), 5.46 (br s, 1H), 5.21 (br s, 1H), 4.76–4.82 (m, 1H), 4.42–4.48 (m, 1H), 4.28–4.38 (m, 1H), 4.22–4.28 (m, 1H), 3.94–4.04 (m, 2H), 2.54 (br s, 3H), 2.23 (br s, 1H), 0.98 (d, J=7.0, 3H), 0.88 (d, J=7.0, 3H). Elemental analysis for $C_{16}H_{23}N_5O_7S$ o HCl: calc'd: C, 41.25; H, 5.02; N, 15.03; S, 6.88; Cl, 7.61; found: C, 40.57; H, 5.37; N, 13.57; S, 6.16; Cl, 7.29.

Scheme 2

Scheme 2 shows a general procedure for preparing 5-Amino-7-methoxy-3-β-D-ribofuranosylthiazolo[4,5-d]pyrimidin-2-ones and 5,7-Diamino-3-β-D-ribofurnosylthiazolo[4,5-d]pyrimidin-2ones.

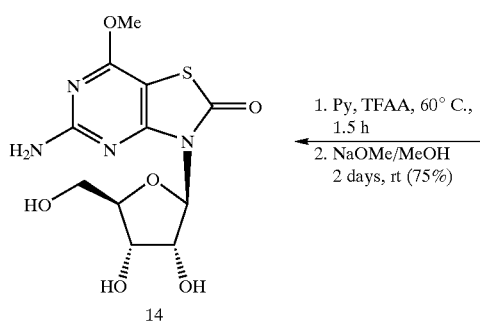

14

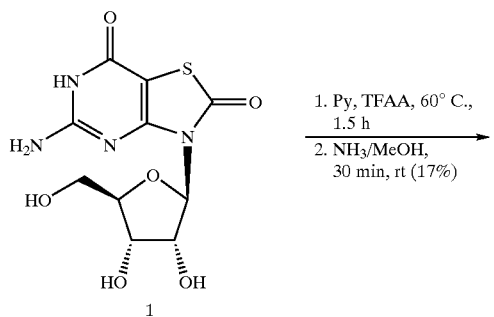

1

EXAMPLE 5

5-Amino-3-β-D-ribofuranosyl-7-methoxy-thiazolo[4,5-d]pyrimidin-2-one (14)

Anhydrous 1 (2.0 g, 6.3 mmol) was dissolved in dry pyridine under an argon atmosphere. The solution was cooled to 0° C., whereupon TFAA (13.3 g, 63 mmol) was added dropwise to the mixture. After five minutes, the reaction was placed in a 60° C. oil bath for 1.5 h, and was monitored by TLC (SiO$_2$, 20% MeOH—CHCl$_3$) for the formation of the pyridinium cation. The 0.2 R$_f$ starting material was converted to a baseline spot that underwent blue fluorescence upon exposure to 254 nm UV light. Upon conversion to the activated intermediate, freshly made sodium methoxide (1.8 g Na, 78 mmol, 300 ml methanol) solution was added to the reaction at 0° C. The reaction was allowed to warm to room temperature and progress for two days. The mixture was then quenched with 1M NH$_4$Cl (100 mL), and extracted with a 25% IPA-CHCl$_3$ (5×100 mL). The crude material was filtered through a silica gel plug, and then concentrated to afford 1.6 g (75%) of the title compound 14. An analytical sample was obtained by preparative TLC (SiO$_2$; water, methanol, ethyl acetate, 5:10:85) as a white solid: mp>160° C. (dec); [M+H]$^+$ 330.9, [2M+H]$^+$ 661.1, [3M+H]$^+$ 991.0; R$_f$=0.6 (20% MeOH—CHCl$_3$); mp 200.4° C.200.9° C.; $^1$H NMR (400 MHz, d$_6$-DMSO) δ 6.92 (s, 2H), 5.86 (d, J=5.2, 1H), 5.28 (d, J=5.6, 1H), 4.96 (d, J=5.2, 1H), 4.78 (dd, J=10.8, 5.6, 1H), 4.67 (t, J=6.0, 1H), 4.07–4.10 (m, 1H), 3.91 (s, 3H), 3.70–3.80 (m, 1H), 3.55–3.60 (m, 1H), 3.40–3.45 (m, 1H). Elemental Analysis for C$_{11}$H$_{14}$N$_4$O$_6$S: calc'd: C, 40.00; H, 4.27; N, 16.96; S, 9.71; found: C, 40.07; H, 4.43; N, 16.71; S, 9.53.

EXAMPLE 6

5,7-Diamino-3-β-D-ribofuranosylthiazolo[4,5-d]pyrimidin-2-one (15)

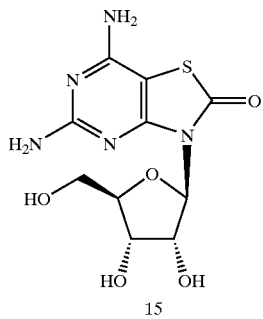

15

Anhydrous 1 (0.3 g, 0.9 mmol) was dissolved in dry pyridine under an argon atmosphere. The solution was cooled to 0° C., then TFAA (1.2 mL, 9.5 mmol) was added dropwise to the mixture. After five minutes, the reaction was placed in a 60° C. oil bath for 1.5 h, and was monitored by TLC (20% MeOH—CHCl$_3$) for the formation of the pyridinium cation. The 0.2 R$_f$ starting material was converted to a baseline spot that underwent blue fluorescence upon exposure to 254 nm UV light. Upon conversion to the activated intermediate, the reaction flask was placed in an ice bath. After allowing the temperature to equilibrate, 30% aqueous NH$_3$ (25 mL) was added dropwise until cessation of exotherm, and the remainder was added. Within a few minutes, the product formed as indicated by analytical TLC R$_f$ 0.25 (SiO$_2$, 20% MeOH—CHCl$_3$). The flask was warmed to room temperature over 30 min, then the aqueous solution was degassed under rotary vacuum then extracted with 25% IPA-CHCl$_3$ (5×100 mL). The product was submitted to flash chromatography (SiO$_2$, 10% MeOH—CHCl$_3$), yielding 55 mg (17%) of slightly impure title compound 15. An analytical sample was obtained by preparative TLC (SiO$_2$; water-MeOH-EtOAc, 5:10:85) as a white solid: mp>155° C. (dec); [M+H]$^+$ 316.0; R$_f$=0.25 (SiO$_2$, 20% MeOH—CHCl$_3$); $^1$H NMR (400 MHz, d$_6$-DMSO) δ 6.76 (s, 2H), 6.14(s, 2H), 5.85 (d, J=5.2, 1H), 5.22 (d, J=4.8, 1H), 4.92 (d, J=2.8, 1H), 4.70–4.83 (m, 2H), 4.05–4.10 (m, 1H), 3.65–3.80 (m, 1H), 3.52–3.62 (m, 1H) 3.40–3.50 (m, 1H). Elemental Analysis for C$_{10}$H$_{13}$N$_5$O$_5$S ·½H$_2$O: calc'd: C, 37.03; H, 4.35; N, 21.59; S, 9.89; found: C, 37.27; H, 4.32; N, 20.43; S, 10.11.

Scheme 3.3

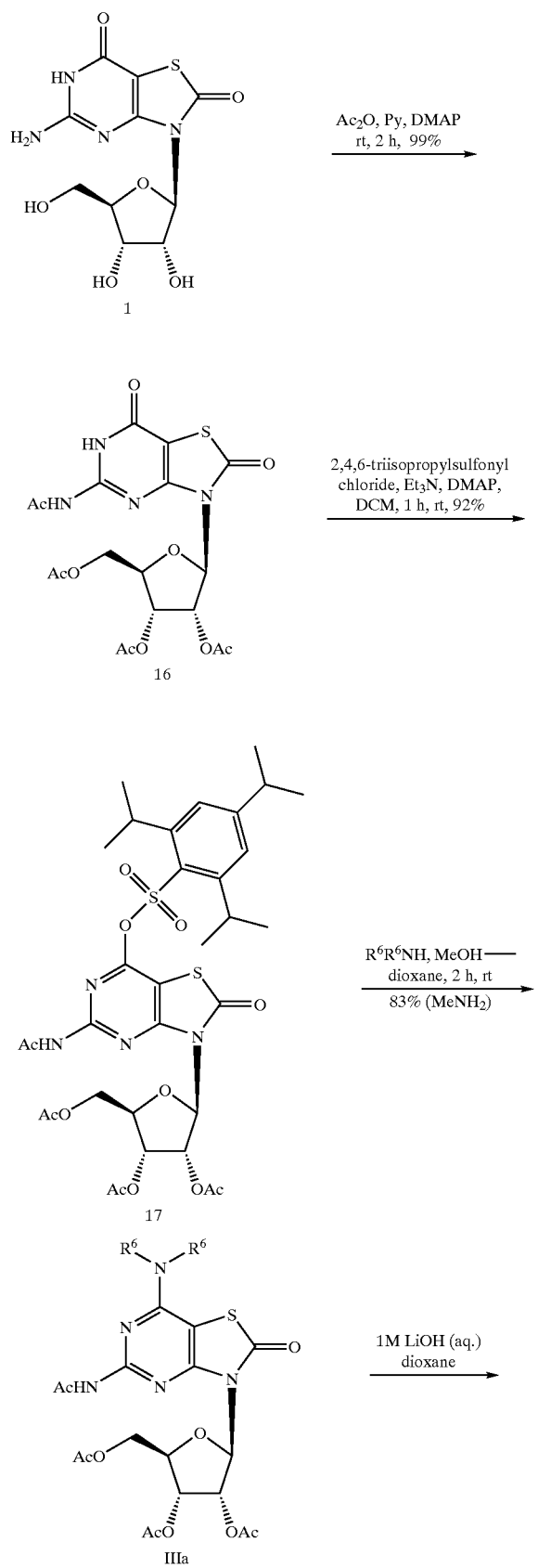

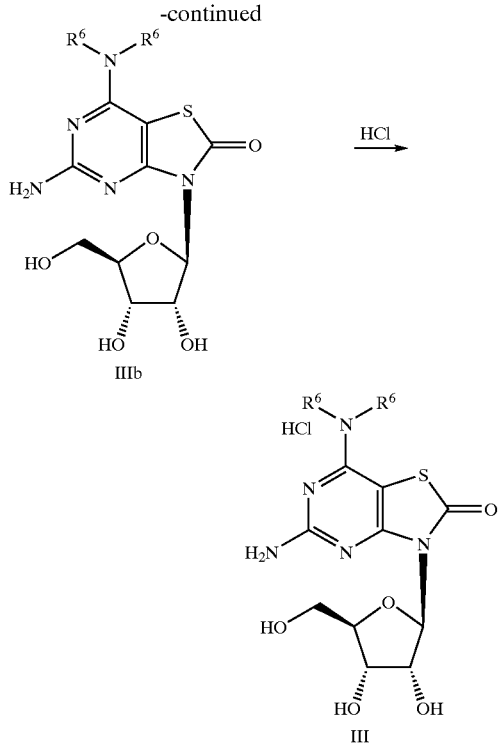

IIIb

III

EXAMPLE 7

5-Amino-7-Methylamino-3-β-D-ribofuranosyl)
thiazolo[4,5-d]pyrimidin-2-one (18)

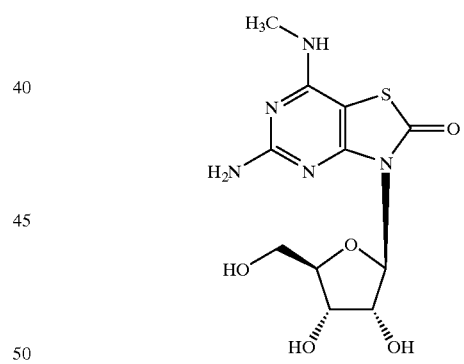

Step 1: Preparation of 5-Acetylamino-3-(2',3',5'-tri-O-acetyl-β-D-ribofuranosyl)thiazolo[4,5-d]pyrimidine-2,7 (6H)-dione (16)

Anhydrous 1 (8.0 g, 39.5 mmol) was dissolved in dry pyridine (65 mL). DMAP (3.1 g, 25.3 mmol) and acetic anhydride (19.1 mL 202.4 mmol) were added sequentially. The reaction was allowed to progress for 2 h at room temperature, whereupon it was quenched with saturated NaHCO$_3$ (100 mL) and extracted with DCM (3×200 mL). The organic phase was concentrated, and then triturated with ether. This provided 12.5 g (103%) of slightly impure 5-acetylamino-3-(2,3,5-tri-O-acetyl-β-D-ribofuranosyl) thiazolo-[4,5-d]pyrimidin-2,7(6H),-dione as a white solid 16: mp 246.7–248.1° C.; R$_f$=0.20 (SiO$_2$, 50% EtOAc—

CHCl$_3$); $^1$H NMR (400 MHz, d$_6$-DMSO) δ 12.23 (s, 1H), 11.85 (s, 1H), 5.97 (m, 2H), 5.48 (t, J=6, 1H), 4.35–4.40 (m, 1H), 4.25–4.31 (m, 1H), 4.08–4.18 (m, 1H), 2.49 (s, 3H), 2.07 (s, 3H), 2.01 (s, 3H), 2.00 (s, 3H).

Step 2: Preparation of 5-Acetylamino-7-(2,4,6-triisopropyl-benzenesulfonyloxy)-3-(2,3,5-tri-O-acetyl -β-D-ribofuranosyl)thiazolo[4,5-d]pyrimidin-2-one (17)

The intermediate from Step 1 above (500 mg, 0.98 mmol) was dissolved in DCM (15 mL) at ambient temperature. DMAP (7.3 mg, 0.06 mmol), and TEA (16 ml, 11 mmol) were added to the solution, followed by 2,4,6-triisopropylbenzenesulfonyl chloride (454 mg, 1.5 mmol). After 1 h the reaction had gone to completion, the crude mixture was concentrated, and then purified by flash chromatography (SiO$_2$, 10% EtOAc—CHCl$_3$), affording 690 mg (92%) of 5-acetylamino-7-(2,4,6-triisopropyl-benzenesulfonyloxy)-3-(2',3',5'-tri-O-acetyl-β-D-ribofuranosyl)thiazolo[4,5-d ]pyrimidin-2-one as a foaming white solid 17: 74.5–76.3° C.; R$_f$=0.7 (SiO$_2$, 20% EtOAc—CHCl$_3$); $^1$H (400 MHz, d$_6$-DMSO) δ 10.83 (s, 1H), 7.39 (s, 2H), 6.03 (d, J=4.0, 1H), 5.91–5.96 (m, 1H), 5.69 (t, J=6.4, 1H), 4.30–4.70 (m, 1H), 4.22–4.26 (m, 1H), 4.16–4.20 (m, 1H), 3.90–4.00 (m, 2H), 2.97–3.01 (m, 1H), 2.07 (s, 3H), (s, 3H), 2.04 (s, 3H), 1.88 (s, 3H), 1.17–1.25 (m, 18H).

Step 3: Preparation of 5-Acetylamino-7-methylamino-3-(2', 3',5'-tri-O-acetyl-β-D-ribofuranosyl)thiazolo[4,5-d]pyrimidin-2-one (19)

The intermediate from Step 2 above (1.7 g, 2.27 mmol) was dissolved in dioxane (20 mL) at ambient temperature. Added to this was a 2.0 M solution of methylamine (3.4 mL, 6.8 mmol) in methanol. After 2 h the starting material was consumed. The reaction mixture concentrated, and then purified by flash chromatography (SiO$_2$, gradient elution, 20–80% EtOAc—CHCl$_3$), affording 945 mg (83%) of pure title compound as a yellow oil: [M+H]$^+$ 498.2, [2M+H]$^+$ 995.4; R$_f$=0.55 (10% CH$_3$OH—CHCl$_3$); $^1$H NMR (400 MHz, d$_6$-DMSO) δ 10.13 (s, 1H), 7.70 (d, J=4.41, 1H), 5.95–6.02 (m, 2H), 5.69 (s, 1H), 4.35–4.39 (m, 1H), 4.16–4.23 (m, 2H), 2.90 (d, J=4.8, 3H), 2.20 (s, 3H), 2.07 (s, 3H), 2.02 (s, 3H), 2.00 (s, 3H).

Step 4: Preparation of 5-Amino-7-Methylamino-3-β-D-ribofuranosyl)thiazolo[4,5-d]pyrimidin-2-one (18)

The intermediate from step 3 above (420 mg, 0.85 mmol) was dissolved in dioxane (4 mL), and 1 M LiOH (8.5 mL, 8.5 mmol) was added to the solution. The O-acetyl groups were removed within 40 min to give a intermediate at R$_f$=0.15 (SiO$_2$, 5% MeOH-EtOAc). After 2 h the N-acetyl was removed as indicated by TLC R$_f$=0.20 (SiO$_2$, 5% MeOH-EtOAc). The reaction mixture was neutralized with stoichiometric acetic acid, extracted with 25% IPA-CHCl$_3$, and then concentrated to afford 195 mg (70%) of 18. An analytical sample of the title compound 18 was obtained by preparative TLC (SiO$_2$; water-MeOH-EtOAc, 10:20:70) as a white solid: [M+H]$^+$ 330.0; R$_f$=0.20 (5% MeOH-EtOAc); mp>108° C.; $^1$H NMR (400 MHz, d$_6$-DMSO) δ 7.06 (d, J=3.6, 1H), 6.24 (s, 2H), 5.85 (d, J=5.2, 1H), 5.22 (d, J=4.8, 1H), 4.93 (d, J =5.2, 1H), 4.70–4.80 (m, 2H), 4.07 (d, J=4.8, 1H), 3.75 (d, J=4.4, 1H), 3.5–3.6 (m, 1H), 3.40–3.50 (m, 1H), 2.82 (d, J=4.4, 3H).

EXAMPLE 8

5-Amino-7-dimethylamino-3-β-D-ribofuranosylthiazolo[4,5-d]pyrimidin-2-one (20)

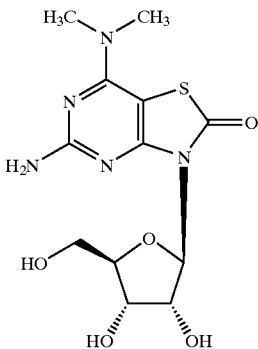

Step 1: Preparation of 5-Acetylamino-7-dimethylamino-3-(2',3',5'-tri-O-acetyl-β-D-ribofuranosyl)thiazolo[4,5-d]pyrimidin-2-one In a manner similar to Example 7, step 2, 5-acetylamino-7-dimethylamino-3-(2',3',5'-tri-O-acetyl-β-D-ribofuranosyl)-thiazolo[4,5-d]pyrimidin-2was generated in an 80% yield as a yellow oil: M$^+$ 511.14; R$_f$=0.70 (SiO$_2$, 10% MeOH—CHCl$_3$); $^1$H NMR (400 MHz, d$_6$-DMSO) δ 10.15 (s, 1H), 6.10–6.15 (m, 1H), 5.98–6.09 (m, 1H), 5.5.66–5.70 (m, 1H), 4.35–4.40 (m, 1H), 4.22–4.27 (m, 1H), 4.14–4.08 (m, 1H), 3.18 (s, 6H), 2.19 (s, 3H), 2.08 (s, 3H), 2.06 (s, 3H), 1.99 (s, 3H).

Step 2: Preparation of 5-Amino-7-dimethylamino-3-β-D-ribofuranosylthiazolo[4,5-d]pyrimidin-2-one (20)

In a manner similar to Example 7, step 3, the title compound 20 was generated in 82% yield. An analytical sample was obtained by preparative TLC (SiO$_2$; water-MeOH-EtOAc, 10:20:70) as a white solid: [M+H]$^+$ 344.0; [2M+H]$^+$ 687.4; mp>112° C; R$_f$=0.20 (5% MeOH-EtOAc); $^1$H NMR (400 MHz, d$_6$-DMSO) δ 6.27 (s, 2H), 5.91 (d, J=4.8, 1H), 5.22 (d, J=6.0, 1H), 4.93 (d, J=5.2, 1H), 4.71–4.76 (m, 2H), 4.07–409 (m, 1H), 3.7–3.8 (m, 1H), 3.5–3.6 (m, 1H), 3.5–3.6 (m, 1H), 3.09 (s, 6H). Elemental analysis for C$_{12}$H$_{17}$N$_5$O$_5$S: calc'd: C, 41.98; H, 4.99; N, 20.40; found: C, 41.32; H, 5.14; N, 18.59.

EXAMPLE 9

5-Amino-7-cyclopropylamino-3-β-D-ribofuranosylthiazolo[4,5-d]pyrimidin-2-one Monohydrochloride Salt (21)

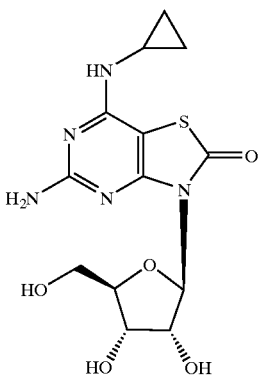

Step 1: Preparation of 5-Acetylamino-7-cyclopropylamino-3-(2',3',5'-tri-O-acetyl-β-D-ribofuranosyl)-thiazolo[4,5-d]pyrimidin-2-one In a manner similar to Example 3, step 2, 5-acetylamino-7-cyclopropylamino-3-(2',3',5'-tri-O-acetyl-β-D-ribofuranosyl)-thiazolo[4,5-d]pyrimidin-2-one was generated in 80% yield as a yellow oil: $R_f$=0.45 (SiO$_2$, 75% EtOAc—CHCl$_3$); $^1$H NMR (400 MHz, d$_6$-DMSO) δ 10.11 (s, 1H), 7.87 (d, J=2.8, 1H), 5.98–6.01 (m, 1H), 5.70–5.76 (s, 1H), 4.32–4.39 (m, 1H), 4.16–4.30 (m, 2H), 3.85 (s, 1H), 2.87 (s, 1H), 2.25 (s, 3H), 2.07 (s, 3H), 2.06 (s, 3H), 1.98 (s, 3H), 0.73–0.76 (m, 2H), 0.57–0.60 (m, 2H).

Step 2: Preparation of 5-Amino-7-cyclopropylamino-3-β-D-ribofuranosylthiazolo[4,5-d]pyrimidin-2-one In a manner similar to Example 7, step 3, 5-amino-7-cyclopropylamino-3-β-D-ribofuranosylthiazolo[4,5-d]pyrimidin-2-one was generated in 79% yield. An analytical sample was obtained by preparative TLC (SiO$_2$; water-MeOH-EtOAc, 10:20:70) as a white solid: $R_f$=0.20 (5% MeOH-EtOAc); mp>100° C.; [M+H]$^+$ 356.0; $^1$H (400 MHz, d$_6$-DMSO) δ 7.24 (s, 1H), 6.28 (s, 2H), 5.86 (d, J=5.6, 1H), 5.22 (d, J=6, 1H) 4.92 (d, J=5.2, 1H), 4.70–4.80 (m, 2H), 4.05–4.10 (m, 1H), 3.7–3.8 (m, 1H), 3.5–3.6 (m, 1H), 3.45–3.50 (m, 1H), 2.8 (s, 1H), 0.68–0.70 (m, 2H), 0.54–0.57 (m, 2H).

Step 3: Preparation of 5-Amino-7-cyclopropylamino-3-β-D-ribofuranosylthiazolo[4,5-d]pyrimidin-2-one Hydrochloride Salt (21)

The title compound was prepared by addition of the solid material prepared in step 2 above to vigorously stirring 4 M HCl in dioxane, affording the title compound as a white solid: mp>99° C.; $^1$H NMR (400 MHz, d$_6$-DMSO) δ 7.25 (d, 1H, J=2.8, 1H), 6.23 (s, 2H), 5.87 (d, J=5.2, 1H), 5.21 (bs, 1H), 4.98 (bs, 1H), 4.73–4.79 (m, 2H), 4.09 (t, J=5.6, 1H), 3.72–3.79 (m, 1H), 3.55–3.60 (m, 1H), 3.45–3.37 (m, 1H), 2.75–2.82 (m, 1H), 0.72–0.79 (m, 2H), 0.55–0.63 (m, 2H). Elemental analysis for C$_{13}$H$_{17}$N$_5$O$_5$S.HCl: calc'd: 39.85; H, 4.63; N, 17.87; Cl, 9.05; found: C, 39.66; H, 4.85; N, 16.57; Cl, 8.13.

EXAMPLE 10

5-Amino-7-cyclopentylamino-3-β-D-ribofuranosylthiazolo[4,5-d]pyrimidin-2-one (22)

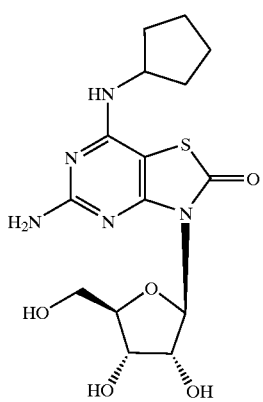

Step 1: Preparation of 5-Acetylamino-7-pyrrolidino-3-(2',3',5'-tri-O-acetyl-β-D-ribofuranosyl)-thiazolo[4,5-d]pyrimidin-2-one In a manner similar to Example 7, step 2, 5-acetylamino-7-pyrrolidino-3-(2',3',5'-tri-O-acetyl-β-D-riboduranosyl)-thiazolo[4,5-d]pyrimidin-2one was generated 70% yield. An analytical sample was obtained via preparative TLC (SiO$_2$; water-MeOH-EtOAc, 10:20:70) as a white solid: mp>108° C. (dec); $R_f$=0.80 (10% water and 20% methanol in ethyl acetate); [M+H]$^+$ 384.0; $^1$H NMR (400 MHz, d$_6$-DMSO) δ 7.00 (d, J=7.2, 1H), 6.17 (s, 2H), 5.18 (d, J=5.2, 1H), 5.21 (d, J=5.6, 1H), 4.92 (d, J =5.6, 1H), 4.74–4.80 (m, 2H), 4.30–4.35 (m, 1H), 4.05–4.10 (m, 1H), 3.70–3.80 (m, 1H), 3.55–3.60 (m, 1H), 3.30–3.45 (m, 1H), 1.40–2.0 (m, 8H).

Step 2: Preparation of 5-Amino-7-cyclopentylamino-3-β-D-ribofuranosylthiazolo[4,5-d]pyrimidin-2-one In a manner similar to Example 7, step 3, the title compound 22 was generated in 70% yield. An analytical sample was obtained via preparative TLC (SiO$_2$; water-MeOH-EtOAc, 10:20:70) as a white solid: mp>108° C. (dec); $R_f$=0.80 (10% water and 20% methanol in ethyl acetate); [M+H]$^+$ 384.0; $^1$H NMR (400 MHz, d$_6$-DMSO) δ 7.00 (d, J=7.2, 1H), 6.17 (s, 2H), 5.18 (d, J=5.2, 1H), 5.21 (d, J=5.6, 1H), 4.92 (d, J=5.6, 1H), 4.74–4.80 (m, 2H), 4.30–4.35 (m, 1H), 4.05–4.10 (m, 1H), 3.70–3.80 m, 1H), 3.55–3.60 (m, 1H), 3.30–3.45 (m, 1H), 1.40–2.0 (m, 8H).

EXAMPLE 11

5-Amino-7-pyrrolidino-3-β-D-ribofuranosylthiazolo[4,5-d]pyrimidin-2-one (23)

Step 1): Preparation of 5-Acetylamino-7-pyrrolidino-3-(2',3',5'-tri-O-acetyl-β-D-ribofuranosyl)thiazolo[4,5-d]pyrimidin-2-one In a manner similar to Example 7, step 2, 5-acetylamino-7-pyrrolidino-3-(2,3,5-tri-O-acetyl-β-D-ribofuranosyl)-thiazolo[4,5-d]pyrimidin-2-one was generated in 79% yield as a yellow oil: [M+H]$^+$ 538.1; $R_f$=0.80 (SiO$_2$, water-MeOH-EtOAc, 10:20:70); $^1$H (400 MHz, d$_6$-DMSO) δ 10.04 (s, 1H), 5.97–6.02 (m, 2H), 5.68 (s, 1H), 4.38 (dd,J= 11.6, 3.6, 1H), 4.15–4.23 (m, 2H), 3.58 (s, 4H), 2.23 (s, 3H), 2.08 (s, 3H), 2.05 (S, 3H), 1.98 (s, 3H), 1.89 (s, 4H).

Step 2: Preparation of 5-Amino-7-pyrrolidino-3-β-D-ribofuranosylthiazolo[4,5-d]pyrimidin-2-one In a manner similar to Example 7, step 3, the title compound 23 was generated in 81% yield. An analytical sample was obtained via preparative TLC (SiO$_2$; water- MeOH-EtOAc, 10:20:70) as a white solid: mp>112.4° C. (dec); [M+H]+ 370.3; ¹H NMR (400 MHz, $d_6$-DMSO) δ 6.22 (s, 2H), 5.90 (d, J=4.8, 1H), 5.23 (d, J=5.2, 1H), 4.94 (d, J=4.4, 1H), 4.68–4.75 (m, 2H), 4.08 (d, J=4.8, 1H), 3.71–3.76 (m, 1H), 3.55 (bs, 5H), 3.38–3.54 (m, 1H), 1.87 (s, 4H).

Scheme 4

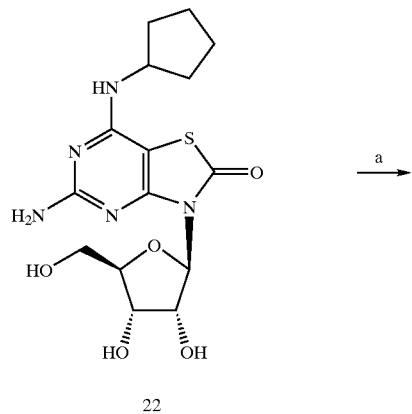

22

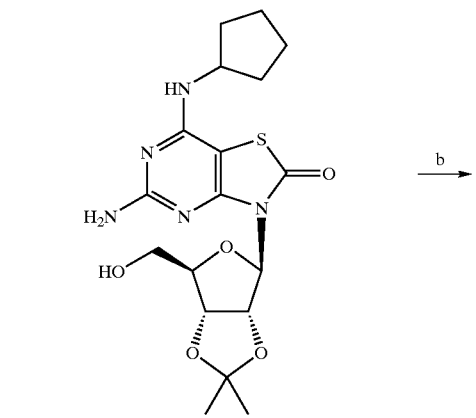

Kini et al,
*JMC*, 34, 3006–3010 (1981)
A

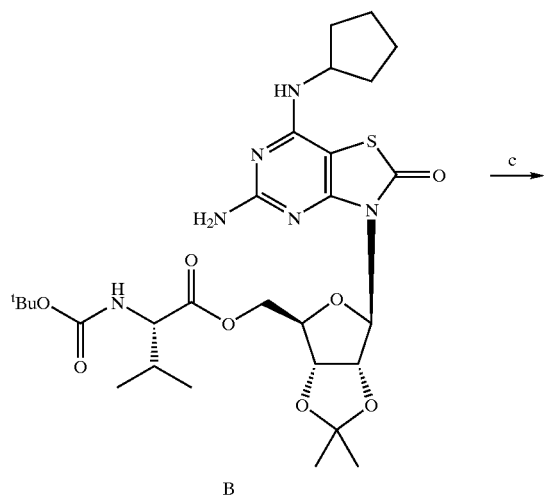

B

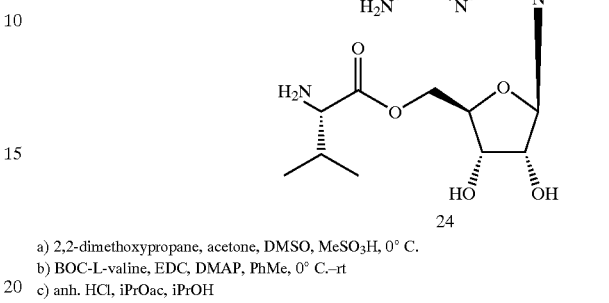

24 a) 2,2-dimethoxypropane, acetone, DMSO, MeSO₃H, 0° C.
b) BOC-L-valine, EDC, DMAP, PhMe, 0° C.–rt
c) anh. HCl, iPrOAc, iPrOH

EXAMPLE 12

5-Amino-7-cyclopentylamino-3-(5'-O-L-valinyl)-β-D-ribofuranosyl)thiazolo[4,5-d]pyrimidin-2-one Hydrochloride (24)

With vigorous stirring, intermediate B is dissolved in a solution of anhydrous hydrogen chloride in isopropyl acetate at 0° C. and allowed to warm to room temperature. To the heterogeneous mixture is added additional isopropyl acetate. The reaction mixture is stirred for an additional 12 h. Toluene is added and the product is filtered and dried under vacuum to yield the desired di-HCl salt 24.

The intermediates are prepared as follows:

5-Amino-7-cyclopentylamino-3-(2',3'-O-isoproylidene-β-D-ribofuranosyl)thiazolo[4,5-d]pyrimidine-2-one (A)

Compound A is prepared according to the procedure of Kini et al., by stirring a mixture of 5-amino-7-cyclopentylamino-3-β-D-ribofuranosylthiazolo[4,5-d]pyrimidine-2-one 22 with acetone, DMSO, methanesulfonic acid and an excess of dimethoxypropane at 0° C. until starting material is consumed. The reaction mixture is added to ice water and neutralized to pH 7 with saturated NaHCO₃ and extracted with EtOAc. The organic layer is concentrated and subjected to column chromatography on silica providing the 2',3'-protected diol product.

5-Amino-7-cyclopentylamino-3-(5'-O-(N-(tert-butoxycarbonyl)-L-valinyl)-2',3'-O-isoproylidene-β-D-ribofuranosyl)thiazolo[4,5-d]pyrimidine-2-one (B)

To a solution of 1.0 equivalents of N-(tert-butoxycarbonyl)-L-valine in THF at 0° C. is added 1.1 equivalents of EDC. After stirring for 30 min. 1.0 equivalent of 5-amino-7-cyclopentyl-3-(2',3'-O-isoproylidene-β-D-ribofuranosyl)thiazolo[4,5-d]pyrimidine-2-one, A, and 1.5 equivalents DMAP are added. The reaction mixture is warmed to room temperature and allowed to stir for 5 h, and concentrated. The residue is dissolved in EtOAc, partitioned with 1 N HCl, and neutralized with saturated aqueous NaHCO₃ (10 mL). The aqueous aqueous phase is further extracted with EtOAc. The combined organic phases are dried over Na₂SO₄, filtered, and evaporated under vacuum to give intermediate B that is purified by column chromatography on silica.

Biological Testing

The ability of compounds of Formula I to demonstrate favorable oral delivery characteristics and to induce immune responses when administered by a selected route was readily demonstrated in experiments in mice and beagle dogs. The results of such measurements for compounds of Formula I can be compared with the results of similar experiments with compounds described in the literature referenced in the present disclosure (e.g., U.S. Pat. Nos. 5,041,426 and 4,880,784) to reveal the advantages of Formula I compounds with respect to pharmacokinetic and pharmacodynamic properties.

Interferon Alpha (Mu-IFN-α) Concentrations in Mice

The normal mouse provides a useful system for the assessment of the degree to which the inventions described herein provide material improvement in the oral delivery of 1 (isatoribine). Not only can one measure the plasma concentrations of isatoribine arising from oral administration of the said prodrug(s) but also the extensive immunological research conducted in the mouse has provided reagents suitable for measuring the levels of interferon alpha, a cytokine of interest reflecting one of the desired biologic activities of isatoribine.

We have used the murine system in a series of experiments that demonstrate that 3, the 5'-valine ester of 1 (val-isatoribine) elicits an interferon response substantially improved over that resulting from administration of isatoribine itself.

Table 1 records the results of an assay for murine interferon alpha in the plasma of mice that were dosed two times with isatoribine, formulated in bicarbonate, at a level of 50 mg/kg by the oral route. It is evident that no interferon was measurable even when the dose was repeated after an interval of four hours.

TABLE 1

Interferon Alpha (Mu-IFN-α) Plasma Concentration (pg/mL) in Mice Following Two Oral 50 mg/kg Doses of Isatoribine 4 Hours Apart

| Time, h | Individual Value | | | Mean | SD |
|---|---|---|---|---|---|
| | First Dose | | | | |
| 0.00 | $BQL^{50}$ | $BQL^{125}$ | $BQL^{50}$ | 0.00 | 0.00 |
| 0.03 | $BQL^{25}$ | $BQL^{250}$ | $BQL^{25}$ | 0.00 | 0.00 |
| 0.08 | $BQL^{25}$ | $BQL^{25}$ | $BQL^{25}$ | 0.00 | 0.00 |
| 0.25 | $BQL^{50}$ | $BQL^{25}$ | $BQL^{25}$ | 0.00 | 0.00 |
| 0.50 | $BQL^{25}$ | $BQL^{25}$ | $BQL^{25}$ | 0.00 | 0.00 |
| 1.00 | $BQL^{25}$ | $BQL^{25}$ | $BQL^{25}$ | 0.00 | 0.00 |
| 1.50 | $BQL^{100}$ | $BQL^{25}$ | $BQL^{25}$ | 0.00 | 0.00 |
| 2.00 | $BQL^{25}$ | $BQL^{75}$ | $BQL^{25}$ | 0.00 | 0.00 |
| 3.00 | $BQL^{25}$ | $BQL^{25}$ | $BQL^{25}$ | 0.00 | 0.00 |
| 4.00 | $BQL^{25}$ | $BQL^{25}$ | $BQL^{25}$ | 0.00 | 0.00 |
| | Second Dose | | | | |
| 4.03 | $BQL^{25}$ | $BQL^{25}$ | $BQL^{25}$ | 0.00 | 0.00 |
| 4.08 | $BQL^{25}$ | $BQL^{25}$ | $BQL^{25}$ | 0.00 | 0.00 |
| 4.25 | $BQL^{25}$ | $BQL^{25}$ | $BQL^{25}$ | 0.00 | 0.00 |
| 4.50 | $BQL^{50}$ | $BQL^{37.5}$ | $BQL^{50}$ | 0.00 | 0.00 |
| 5.00 | $BQL^{50}$ | $BQL^{50}$ | $BQL^{50}$ | 0.00 | 0.00 |
| 5.50 | $BQL^{37.5}$ | $BQL^{37.5}$ | $BQL^{37.5}$ | 0.00 | 0.00 |
| 6.00 | $BQL^{50}$ | $BQL^{41.3}$ | $BQL^{37.5}$ | 0.00 | 0.00 |
| 7.00 | $BQL^{50}$ | $BQL^{50}$ | $BQL^{59}$ | 0.00 | 0.00 |
| 8.00 | $BQL^{50}$ | $BQL^{25}$ | $BQL^{50}$ | 0.00 | 0.00 |

$BQL^n$—Below Elevated Quantifiable Limit < n pg/mL.

Table 2 records the results of assays for murine interferon alpha in the plasma of mice that first were dosed with bicarbonate and then four hours later were dosed orally with isatoribine, formulated in bicarbonate, at a level of 50 mg/kg. Interferon was reported in the plasma from four mice, including two that had received the bicarbonate vehicle dose. All the values reported in this experiment were low, and the reported interferon levels were not consistently reported for all three mice assessed at each time point, suggesting that these signals may be artifacts arising from measurement near the lower limits of the assay.

TABLE 2

Interferon Alpha (Mu-IFN-α) Plasma Concentration (pg/mL) in Mice Following One Vehicle Dose and One 50 mg/kg Doses of Isatoribine 4 Hours Later

| Time, h | Individual Value | | | Mean | SD |
|---|---|---|---|---|---|
| | First Dose | | | | |
| 0.00 | $BQL^{50}$ | $BQL^{100}$ | $BQL^{62.5}$ | 0.00 | 0.00 |
| 0.03 | $BQL^{50}$ | $BQL^{50}$ | $BQL^{37.5}$ | 0.00 | 0.00 |
| 0.08 | $BQL^{50}$ | $BQL^{50}$ | $BQL^{50}$ | 0.00 | 0.00 |
| 0.25 | $BQL^{50}$ | $BQL^{62.5}$ | $BQL^{50}$ | 0.00 | 0.00 |
| 0.50 | $BQL^{50}$ | $BQL^{50}$ | $BQL^{50}$ | 0.00 | 0.00 |
| 1.00 | $BQL^{50}$ | $BQL^{50}$ | $BQL^{100}$ | 0.00 | 0.00 |
| 1.50 | $BQL^{50}$ | $BQL^{100}$ | $BQL^{50}$ | 0.00 | 0.00 |
| 2.00 | 34.9 | $BQL^{25}$ | $BQL^{25}$ | 11.6 | 20.15 |
| 3.00 | $BQL^{25}$ | $BQL^{25}$ | $BQL^{25}$ | 0.00 | 0.00 |
| 4.00 | $BQL^{25}$ | 35.4 | $BQL^{100}$ | 11.8 | 20.44 |
| | Second Dose | | | | |
| 4.03 | $BQL^{25}$ | $BQL^{25}$ | $BQL^{25}$ | 0.00 | 0.00 |
| 4.08 | $BQL^{25}$ | $BQL^{25}$ | $BQL^{25}$ | 0.00 | 0.00 |
| 4.25 | $BQL^{25}$ | $BQL^{25}$ | $BQL^{25}$ | 0.00 | 0.00 |
| 4.50 | $BQL^{100}$ | $BQL^{25}$ | 133.2 | 44.4 | 76.90 |
| 5.00 | 74.9 | $BQL^{50}$ | NR | 37.5 | 52.96 |
| 5.50 | $BQL^{250}$ | $BQL^{75}$ | $BQL^{25}$ | 0.00 | 0.00 |
| 6.00 | $BQL^{25}$ | $BQL^{75}$ | $BQL^{75}$ | 0.00 | 0.00 |
| 7.00 | $BQL^{50}$ | $BQL^{50}$ | $BQL^{25}$ | 0.00 | 0.00 |
| 8.00 | $BQL^{25}$ | $BQL^{25}$ | $BQL^{25}$ | 0.00 | 0.00 |

$BQL^n$—Below Elevated Quantifiable Limit < n pg/mL.
NR—Not reportable.

Table 3 records the results of assays for murine interferon alpha in the plasma of mice that were dosed orally with val-isatonibine, dissolved in bicarbonate, at a dose that is equivalent to 50 mg/kg of isatoribine on a molar basis. It is evident that interferon was readily measurable at 1.0 hour, 1.5 hours, and 2.0 hours after dosing. Interferon was detected in all mice assayed at a given time point, indicating the reliability of the effect following val-isatoribine administration. Thus a single administration of val-isatoribine was superior to either a single dose or a repeated dose of isatoribine.

TABLE 3

Plasma Concentration (pg/mL) of Interferon Alpha (Mu-IFN-α) in Mice Following a Single 73.0 mg/kg Dose of Val-Isatoribine

| Time, h | Individual Value | | | Mean | SD |
|---|---|---|---|---|---|
| 0.00 | BQL | $BQL^{125}$ | $BQL^{25}$ | 0.00 | 0.00 |
| 0.25 | BQL | BQL | BQL | 0.00 | 0.00 |
| 0.50 | $BQL^{25}$ | $BQL^{25}$ | BQL | 0.00 | 0.00 |
| 0.75 | BQL | BQL | $BQL^{25}$ | 0.00 | 0.00 |
| 1.00 | 173.2 | 125.1 | 89.0 | 129.1 | 42.24 |
| 1.50 | 202.9 | 145.9 | 294.8 | 214.5 | 75.13 |
| 2.00 | 49.2 | 137.9 | 138.3 | 108.5 | 51.33 |
| 3.00 | $BQL^{25}$ | NR | NR | 0.00 | 0.00 |
| 4.00 | $BQL^{25}$ | 27.6 | BQL | 9.20 | 15.90 |
| 5.00 | BQL | $BQL^{25}$ | $BQL^{25}$ | 0.00 | 0.00 |

BQL—Below the Quantifiable Limit < 12.5 pg/mL
$BQL^n$—Below the Elevated Quantifiable Limit < n pg/mL
NR—Not Reportable The data tabulated in Tables 1, 2, and 3 may be also considered from the point of view of the incidence of measurable interferon levels. Interferon was detected in the plasma of only 4 of the 114 mice used in the studies of isatoribine, whereas 10 of the 30 mice dosed with val-isatoribine had detectable interferon in their plasma. Thus, the prodrug increased the proportion of mice exhibiting an interferon response from 4% to 30% and the magnitude of both the average and peak response was increased twofold.

In other experiments, plasma levels of isatoribine and interferon alpha were measured in mice that were dosed with isatoribine by the intravenous route, and these levels were compared to the levels of isatoribine and interferon alpha arising after oral administration of val-isatoribine. These data are summarized in FIG. 1. In this figure it is evident that the levels of interferon alpha induced by oral val-isatoribine ("val-isator") (at 50 mg/kg isatoribine molar equivalent) was similar to that from intravenous isatoribine ("isator") at 25 mg/kg. Thus, oral val-isatoribine provides levels of isatoribine and interferon that are approximately 50% of those observed after intravenous administration of isatoribine itself.

Beagle Dog The effect of a prodrug (val-isatoribine, 3) on the systemic exposure to isatoribine (1) after oral administration to beagle dogs was investigated. Isatoribine was prepared in sodium bicarbonate solution. Val-isatoribine and isatoribine were prepared as the following formulations, which were chosen to ensure solubility:

Formulation 1: Isatoribine in sodium bicarbonate solution, 1 and 4 mg/mL.

Formulation 2: Val-isatoribine in phosphate buffered saline, 1.62 and 6.48 mg/mL, equivalent to 1 and 4 mg/mL of isatoribine on a molar basis.

Four male and four female adult beagle dogs weighing between 15 to 27 kg and approximately 1–2 years old were used at the beginning of the study. The animals were divided into 2 groups of 2 males and 2 females each. The test material was administered by gavage on Days 1 and 8, allowing a 7-day washout period between administrations. Blood samples (2 mL) were collected from each animal at predose, 15, 30 minutes, 1, 2, 3, 4, 6, 8 and 10 hours into lithium heparin tubes after each dosing. The plasma was frozen at −70° C. until analysis. The plasma was analyzed for isatoribine by an HPLC-MS/MS assay.

The pharmacokinetic parameters for isatoribine arising from isatoribine or val-isatoribine in each dog are summarized in Tables 4 and 5. The ratios for the key pharmacokinetic parameters defining the maximum concentration (Cmax) and total exposure as measured by the area under the time-concentration curve (AUC) for the prodrug and the bicarbonate solution at the 50 mg/kg dose are summarized in Table 6. For the prodrug 3, the Cmax ratio was 2.98±0.695 and the AUC ratio was 2.38±0.485. These results indicate that at 50 mg/kg dose, the prodrug val-isatoribine provided substantially higher Cmax and greater bioavailability than isatoribine in bicarbonate solution.

The ratios for the Cmax and AUC for the prodrug to the bicarbonate solution for the 10 mg/kg dose are summarized in Table 7. For the prodrug, the Cmax ratio was 2.24±0.249 and the AUC ratio was 1.82±0.529. These results indicate that at 10 mg/kg dose, the prodrug val-isatoribine provided higher Cmax and greater bioavailability than isatoribine in bicarbonate solution.

Thus, the maximum concentrations of isatoribine achieved after oral dosing are at least doubled, and the systemic exposure to isatoribine is enhanced by approximately 2-fold following oral administration of the prodrug val-isatoribine, compared to isatoribine itself, at both 10 and 50 mg/kg dose.

TABLE 4

Pharmacokinetic Parameters of Isatoribine in Dogs dosed at 50 mg/kg

| | | 1 | 2 |
|---|---|---|---|
| | Dosing Period Formulation | Isatoribine | Val-isatoribine |
| Animal Number | Dose, mg/kg molar equivalent isatoribine | 50 | 50 |
| Dog 3517322 | Cmax, ng/mL | 3038.7 | 11741.5 |
| | Tmax, h | 0.50 | 0.50 |
| | AUC(0-inf), ng.h/mL | 15227.0 | 33038.1 |
| | $T_{1/2}$, h | 6.4 | 2.4 |
| Dog 3521451 | Cmax, ng/mL | 3354.0 | 10652.1 |
| | Tmax, h | 1.00 | 1.00 |
| | AUC(0-inf), ng.h/mL | 9422.2 | 26552.7 |
| | $T_{1/2}$, h | 1.9 | 1.6 |
| Dog 3528707 | Cmax, ng/mL | 8915.3 | 20340.6 |
| | Tmax, h | 0.50 | 0.50 |
| | AUC(0-inf), ng.h/mL | 29701.7 | 53273.0 |
| | $T_{1/2}$, h | 2.2 | 2.3 |
| Dog 3532828 | Cmax, ng/mL | 6134.7 | 15987.9 |
| | Tmax, h | 0.50 | 0.50 |
| | AUC(0-inf), ng-h/mL | 12069.7 | 32987.0 |
| | $T_{1/2}$, h | 1.4 | 1.6 |

TABLE 5

Pharmacokinetic Parameters of Isatoribine in Dogs Dosed at 10 mg/kg

| | | 1 | 2 |
|---|---|---|---|
| | Dosing Period Formulation | Isatoribine | Val-isatoribine |
| Animal Number | Dose, mg/kg molar equivalent isatoribine | 10 | 10 |
| Dog 3524523 | Cmax, ng/mL | 4091.5 | 8594.6 |
| | Tmax, h | 1.00 | 0.50 |
| | AUC(0-inf), ng.h/mL | 13305.8 | 17166.2 |
| | $T_{1/2}$, h | 2.1 | 1.7 |
| Dog 3526402 | Cmax, ng/mL | 1859.5 | 4047.0 |
| | Tmax, h | 1.00 | 1.00 |
| | AUC(o-inf), ng.h/mL | 5774.4 | 10548.9 |
| | $T_{1/2}$, h | 1.6 | 2.2 |
| Dog 357450 | Cmax, ng/mL | 1620.3 | 4228.7 |
| | Tmax, h | 0.50 | 1.00 |
| | AUC(0-inf), ng.h/mL | 4387.3 | 11158.0 |
| | $T_{1/2}$, h | 1.5 | 2.3 |
| Dog 354708 | Cmax, ng/mL | 2781.2 | 5784.8 |
| | Tmax, h | 0.50 | 0.50 |
| | AUC(o-inf), ng.h/mL | 7522.1 | 12259.1 |
| | $T_{1/2}$, h | 1.6 | 2.0 |

TABLE 6

Ratio of Pharmacokinetic Parameters of Isatoribine in Dogs Dosed at 50 mg/kg

| Animal Number | Formulation | Isatoribine | Val-isatoribine |
|---|---|---|---|
| Dog 3517322 | Cmax Ratio | 1.00 | 3.86 |
| | AUC Ratio | 1.00 | 2.17 |
| Dog 3521451 | Cmax Ratio | 1.00 | 3.18 |
| | AUC Ratio | 1.00 | 2.82 |
| Dog 3528707 | Cmax Ratio | 1.00 | 2.28 |
| | AUC Ratio | 1.00 | 1.79 |
| Dog 3532828 | Cmax Ratio | 1.00 | 2.61 |
| | AUC Ratio | 1.00 | 2.73 |
| | Mean Cmax Ratio | N/A | 2.98 |
| | SD Cmax Ratio | N/A | 0.695 |
| | Mean AUC Ratio | N/A | 2.38 |
| | SD AUC Ratio | N/A | 0.485 |

TABLE 7

Ratio of Pharmacokinetic Parameters of Isatoribine in Dogs Dosed at 10 mg/kg

| Animal Number | Formulation | Isatoribine | Val-isatoribine |
|---|---|---|---|
| Dog 3524523 | Cmax Ratio | 1.00 | 2.10 |
|  | AUC Ratio | 1.00 | 1.29 |
| Dog 3526402 | Cmax Ratio | 1.00 | 2.18 |
|  | AUC Ratio | 1.00 | 2.20 |
| Dog 3527450 | Cmax Ratio | 1.00 | 2.61 |
|  | AUC Ratio | 1.00 | 2.54 |
| Dog 355708 | Cmax Ratio | 1.00 | 2.08 |
|  | AUC Ratio | 1.00 | 1.63 |
|  | Mean Cmax Ratio | N/A | 2.24 |
|  | SD Cmax Ratio | N/A | 0.249 |
| Mean AUC Ratio |  | N/A | 1.82 |
|  | SD AUC Ratio | N/A | 0.529 |

The prodrug is preferred for several reasons. First, the prodrug is easily formulated to provide a high proportion of active agent. This results in small capsule sizes for a given dose, which is an advantage for an oral product. Second, the prodrugs offer the prospect of masking the active structure as the agent passes through lymphoid tissue lining the gut, which should minimize activation of this tissue and thereby improve oral tolerability. Finally, at the doses tested, val-isatoribine provides plasma levels of isatoribine that are well within the range desirable for biologic effect after oral administration, which is not the case for isatoribine itself.

The exemplary compounds described above may be formulated into pharmaceutical compositions according to the following general examples.

EXAMPLE 1

Parenteral Composition

To prepare a parenteral pharmaceutical composition suitable for administration by injection, 100 mg of a water-soluble salt of a compound of the Formula I is dissolved in DMSO and then mixed with 10 mL of 0.9% sterile saline. The mixture is incorporated into a dosage unit form suitable for administration by injection.

EXAMPLE 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

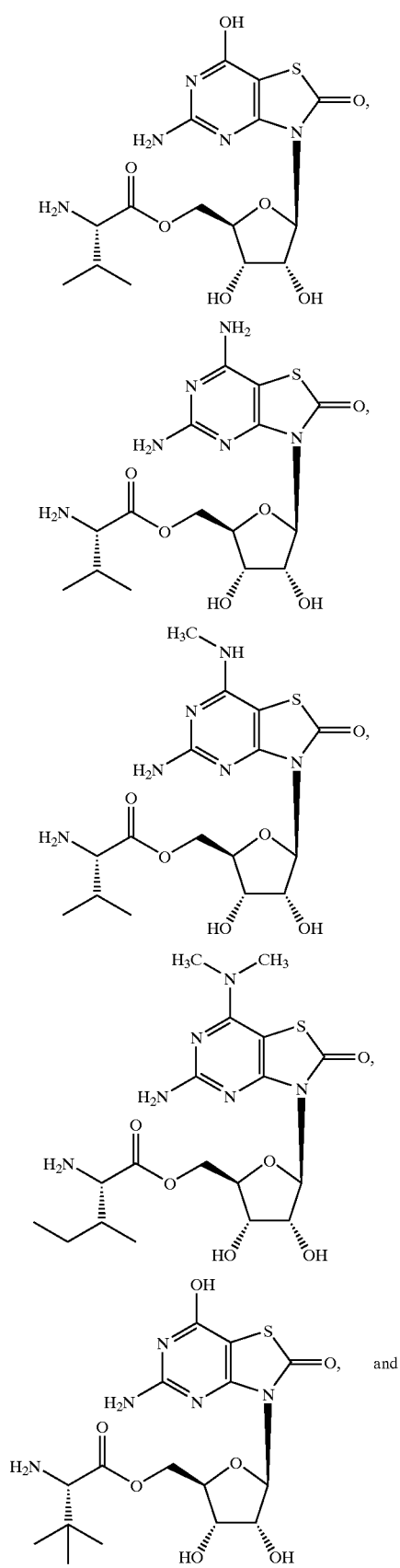
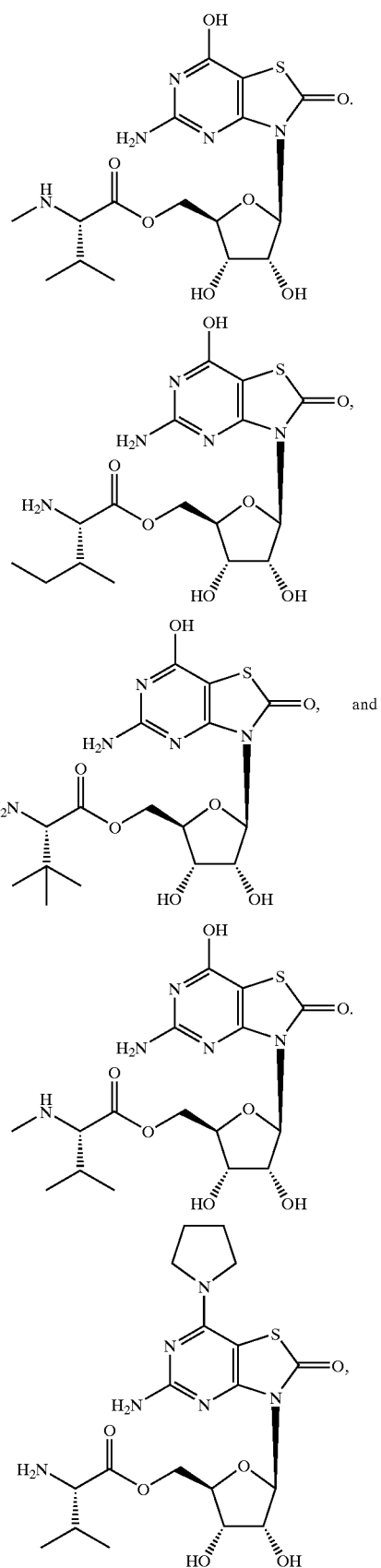

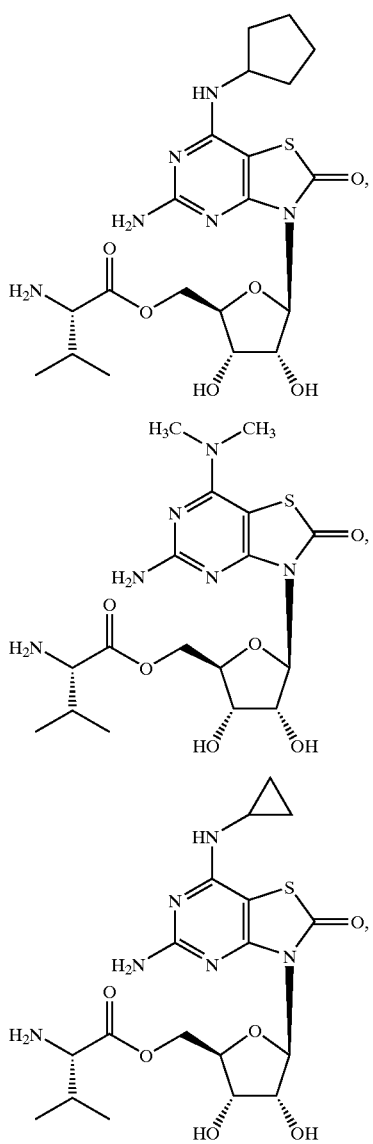
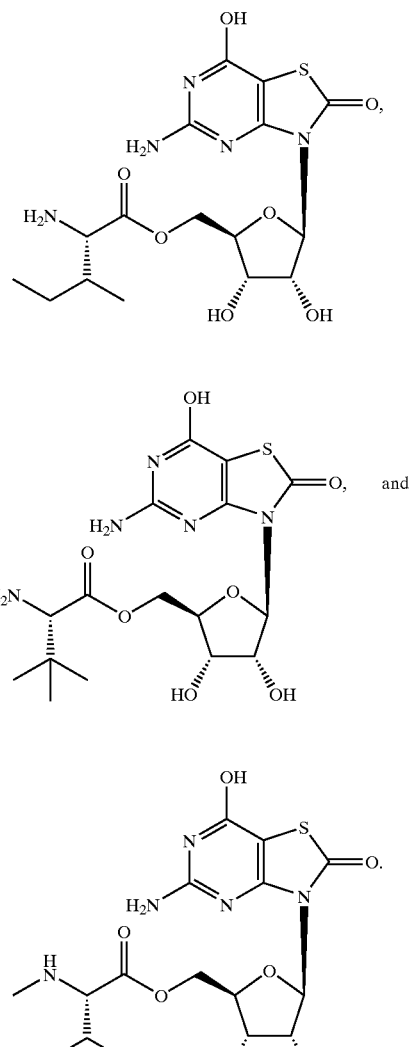

What is claimed is:

1. A compound represented by Formula I:

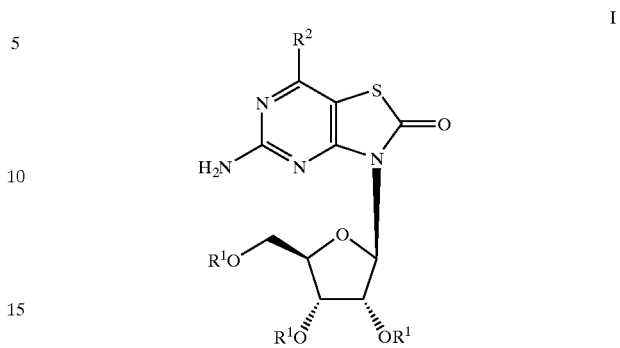

wherein $R^1$ is independently H, —C(O)$R^3$, or a racemic, L-, or D-amino acid group —C(O)CHNH$_2$R$^4$, wherein $R^3$ is alkyl and $R^4$ is H, or alkyl; wherein alkyl is optionally substituted by one or more groups selected from halogen, —C$_1$–C$_6$, —OH, —NO$_2$, —CN, —CO$_2$H, —O—C$_1$–C$_6$, -aryl, -aryl-C$_1$–C$_6$, —CO$_2$CH$_3$, —CONH$_2$, —OCH$_2$CONH$_2$, —NH$_2$, —SO$_2$NH$_2$, haloalkyl, and —O-haloalkyl;

$R^2$ is OR$^5$ or N(R$^6$)$_2$, wherein $R^5$ is H and $R^6$ is independently H, alkyl, cycloalkyl, or together with nitrogen forms a heterocycloalkyl ring, wherein the alkyl, cycloalkyl, and heterocycloalkyl are ontionally substituted by one or more groups selected from halogen, —C$_1$–C$_6$, —OH, —NO$_2$, —CN, —CO$_2$H, —O—C$_1$–C$_6$, -aryl, -aryl-C$_1$–C ($_6$, —CO$_2$CH$_3$, —CONH$_2$, —OCH$_2$CONH$_2$, —NH$_2$, —SO$_2$NH$_2$, haloalkyl, and —O-haloalkyl; and wherein at least one of the $R^1$ groups is a racemic, L-, or D-amino acid group—C(O)CHNH$_2$R$^4$;

or a pharmaceutically acceptable salt.

2. The compound or pharmaceutically acceptable salt according to claim 1, wherein $R^4$ is alkyl, and wherein the remaining $R^1$ groups are H; $R^2$ is OR$^5$ or N(R$^6$)$_2$, wherein $R^5$ is, and wherein $R^6$ is independently H, alkyl, cycloalkyl, or together with nitrogen forms a heterocycloalkyl ring.

3. The compound or pharmaceutically acceptable salt according to claim 2, wherein $R^6$ is independently H or alkyl.

4. The compound or pharmaceutically acceptable salt according to claim 1, wherein $R^4$ is —CH(CH$_3$)$_2$, and wherein the remaining $R^1$ groups are H; and $R^2$ is OH.

5. A compound or pharmaceutically acceptable salt selected from the group consisting of:

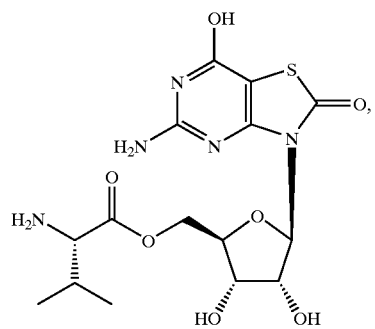

-continued
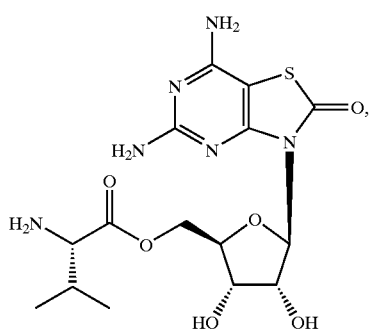
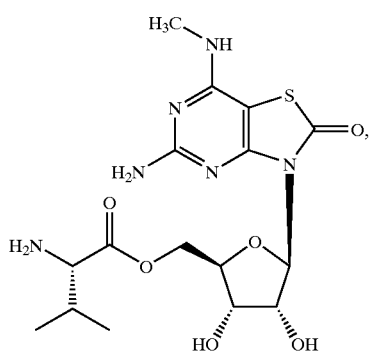
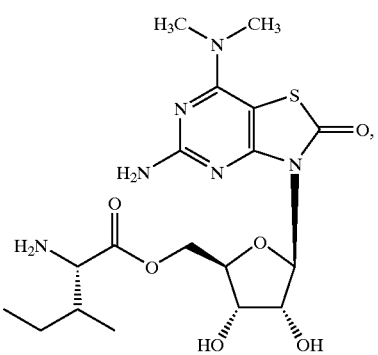
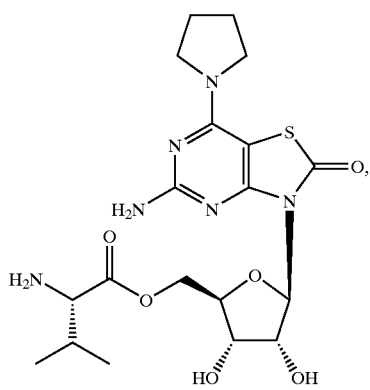
-continued
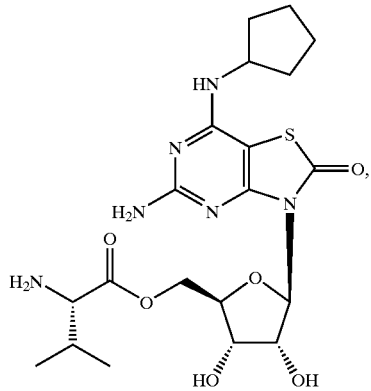
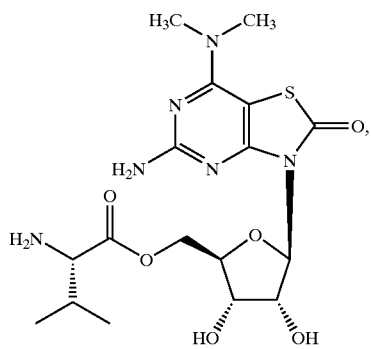
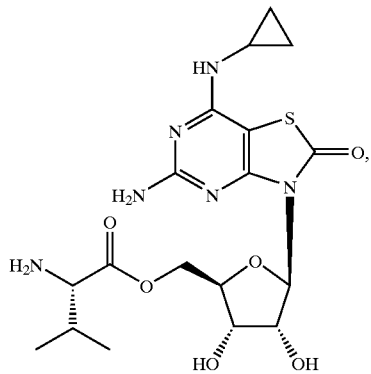
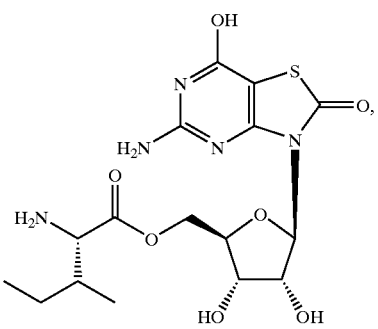

-continued

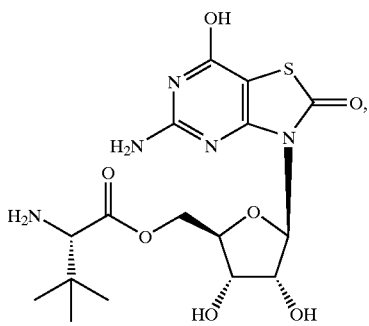

and

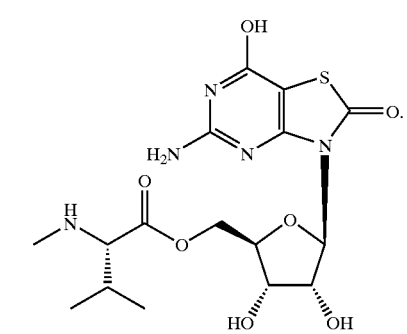

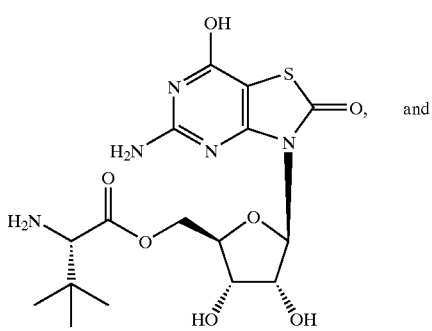

and

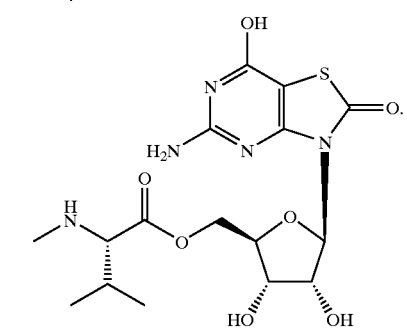

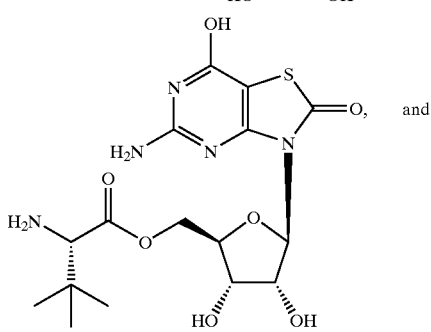

and

-continued

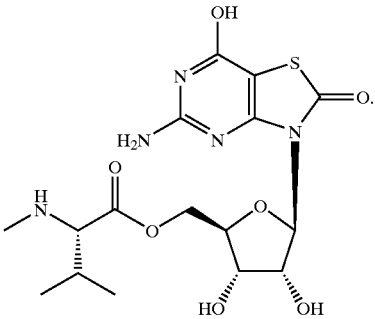

6. A pharmaceutical composition comprising a pharmaceutically acceptable carrier and a compound represented by Formula I:

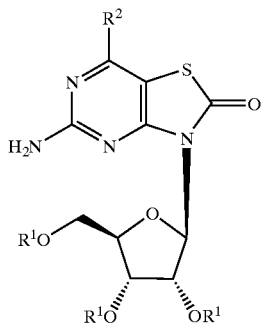

I wherein:

$R^1$ is independently H, —C(O)$R^3$, or a racemic, L-, or D-amino acid group —C(O)CHNH$_2R^4$, wherein $R^3$ is alkyl, and $R^4$ is H or alkyl wherein alkyl is optionally substituted by one or more groups selected from halogen, —C$_1$-C$_6$, —OH, —NO$_2$, —CN, —CO$_2$H, —O—C$_1$-C$_6$, -aryl, -aryl-C$_1$-C$_6$, —CO$_2$CH$_3$, —CONH$_2$, —OCH$_2$CONH$_2$, —NH$_2$, —SO$_2$NH$_2$, haloalkyl, and —O-haloalkyl;

$R^2$ is OR$^5$ or N(R$^6$)$_2$, wherein $R^5$ is and $R^6$ is independently H, alkyl, cycloalkyl, or together with nitrogen forms a heterocycloalkyl ring, wherein the alkyl, cycloalkyl, and heterocycloalkyl are optionally sustituted by one or more groups selected from halogen, —C$_1$-C$_6$, —OH, —NO$_2$, —CN, —CO$_2$H, —O—C$_1$-C$_6$, -aryl, -aryl- C$_1$-C $_6$, —CO$_2$CH$_3$, —CONH$_2$, —OCH$_2$CONH$_2$, —NH$_2$, —SO$_2$NH$_2$, haloalkyl, and —O-haloalkyl; and wherein at least one of the $R^1$ groups is a racemic, L-, or D-amino acid group—C(O)CHNH$_2R^4$;

or a pharmaceutically acceptable salt.

7. The pharmaceutical composition according to claim 6, wherein $R^4$ is alkyl, and wherein the remaining $R^1$ groups are H; $R^2$ is OR$^5$ or N(R$^6$)$_2$, wherein $R^5$ is H, and wherein $R^6$ is independently H, alkyl, cycloalkyl, or together with nitrogen forms a heterocycloalkyl ring.

8. The pharmaceutical composition according to claim 7, wherein $R^6$ is independently H or alkyl.

9. The pharmaceutical composition according to claim 6, wherein $R^4$ is —CH(CH$_3$)$_2$, and wherein the remaining $R^1$ groups are H; and $R^2$ is OH.

10. A pharmaceutical composition according to claim 6, selected from the group consisting of: